(12) United States Patent
Miles et al.

(10) Patent No.: US 7,582,058 B1
(45) Date of Patent: Sep. 1, 2009

(54) SURGICAL ACCESS SYSTEM AND RELATED METHODS

(75) Inventors: Patrick Miles, San Diego, CA (US);
Scot Martinelli, San Diego, CA (US);
Eric Finley, San Diego, CA (US);
James Gharib, San Diego, CA (US);
Allen Farquhar, San Diego, CA (US);
Norbert Kaula, Arvada, CO (US);
Jeffrey Blewett, San Diego, CA (US);
Goretti Medeiros, legal representative, Plantsville, CT (US)

(73) Assignee: NuVasive, Inc., San Diego, CA (US)

( * ) Notice: Subject to any disclaimer, the term of this patent is extended or adjusted under 35 U.S.C. 154(b) by 191 days.

(21) Appl. No.: 10/608,362

(22) Filed: Jun. 26, 2003

Related U.S. Application Data

(60) Provisional application No. 60/392,214, filed on Jun. 26, 2002.

(51) Int. Cl.
*A61B 1/32* (2006.01)
*A61B 5/04* (2006.01)

(52) U.S. Cl. ............... 600/202; 600/214; 600/546; 600/554; 607/2

(58) Field of Classification Search ......... 600/201–207, 600/490, 493–496, 210, 214, 215, 233, 219, 600/554, 546, 221; 606/99; 607/2
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. ............... 128/2.1 |
| 2,736,002 A | 2/1956 | Oriel |
| 2,808,826 A | 10/1957 | Reiner et al. |
| 3,364,929 A | 1/1968 | Ide et al. ................. 128/172.1 |
| 3,664,329 A | 5/1972 | Naylor ................... 128/2.1 R |

(Continued)

FOREIGN PATENT DOCUMENTS

DE 29908259 7/1999

(Continued)

OTHER PUBLICATIONS

"Electromyography System", *International Search Report*, International Application No. PCT/US00/32329,(Apr. 27, 2001), 9 pages.

(Continued)

*Primary Examiner*—Pedro Philogene
(74) *Attorney, Agent, or Firm*—Jonathan Spangler; Rory Schermerhom

(57) ABSTRACT

A system for accessing a surgical target site and related methods, involving an initial distraction system for creating an initial distraction corridor, and an assembly capable of distracting from the initial distraction corridor to a secondary distraction corridor and thereafter sequentially receiving a plurality of retractor blades for retracting from the secondary distraction corridor to thereby create an operative corridor to the surgical target site, both of which may be equipped with one or more electrodes for use in detecting the existence of (and optionally the distance and/or direction to) neural structures before, during, and after the establishment of an operative corridor to a surgical target site.

9 Claims, 33 Drawing Sheets

U.S. PATENT DOCUMENTS

| | | | |
|---|---|---|---|
| 3,682,162 A | 8/1972 | Colyer | 128/2.1 R |
| 3,785,368 A | 1/1974 | McCarthy et al. | 128/2.1 Z |
| 3,830,226 A | 8/1974 | Staub et el. | 128/2.1 R |
| 3,957,036 A | 5/1976 | Normann | 128/2.1 R |
| 4,099,519 A | 7/1978 | Warren | 128/2.1 R |
| 4,164,214 A | 8/1979 | Stark et al. | |
| 4,207,897 A | 6/1980 | Lloyd et al. | 128/303.1 |
| 4,224,949 A | 9/1980 | Scott et al. | 128/734 |
| 4,226,228 A | 10/1980 | Shin et al. | |
| 4,235,242 A | 11/1980 | Howson et al. | 128/695 |
| 4,285,347 A | 8/1981 | Hess | 128/785 |
| 4,291,705 A | 9/1981 | Severinghaus et al. | 600/546 |
| 4,461,300 A | 7/1984 | Christensen | |
| 4,515,168 A | 5/1985 | Chester et al. | 128/741 |
| 4,519,403 A | 5/1985 | Dickhudt | 128/785 |
| 4,545,374 A * | 10/1985 | Jacobson | 606/61 |
| 4,561,445 A | 12/1985 | Berke et al. | 128/642 |
| 4,562,832 A * | 1/1986 | Wilder et al. | 600/223 |
| 4,573,448 A | 3/1986 | Kambin | |
| 4,592,369 A | 6/1986 | Davis et al. | 128/733 |
| 4,595,018 A | 6/1986 | Rantala | 128/733 |
| 4,633,889 A | 1/1987 | Talalla | 128/784 |
| 4,658,835 A | 4/1987 | Pohndorf | 128/785 |
| 4,744,371 A | 5/1988 | Harris | 607/117 |
| 4,759,377 A | 7/1988 | Dykstra | 128/733 |
| 4,784,150 A | 11/1988 | Voorhies et al. | |
| 4,807,642 A | 2/1989 | Brown | 128/733 |
| 4,892,105 A | 1/1990 | Prass | 128/741 |
| 4,926,865 A | 5/1990 | Oman | 128/421 |
| 4,962,766 A | 10/1990 | Herzon | 128/741 |
| 4,964,411 A | 10/1990 | Johnson et al. | 128/733 |
| 5,007,902 A | 4/1991 | Witt | 604/117 |
| 5,058,602 A | 10/1991 | Brody | 128/733 |
| 5,081,990 A | 1/1992 | Deletis | 128/642 |
| 5,092,344 A | 3/1992 | Lee | 128/741 |
| 5,127,403 A | 7/1992 | Brownlee | 128/419 P |
| 5,161,533 A | 11/1992 | Prass et al. | 128/639 |
| 5,196,015 A | 3/1993 | Neubardt | 606/61 |
| RE34,390 E | 9/1993 | Culver | 128/731 |
| 5,255,691 A | 10/1993 | Otten | 607/117 |
| 5,282,468 A | 2/1994 | Klepinski | 128/642 |
| 5,284,153 A | 2/1994 | Raymond et al. | 128/741 |
| 5,284,154 A | 2/1994 | Raymond et al. | 128/741 |
| 5,299,563 A * | 4/1994 | Seton | 600/215 |
| 5,312,417 A | 5/1994 | Wilk | 606/114 |
| 5,313,956 A | 5/1994 | Knutsson et al. | 128/741 |
| 5,327,902 A | 7/1994 | Lemmen | 128/734 |
| 5,333,618 A | 8/1994 | Lekhtman et al. | 128/734 |
| 5,375,067 A | 12/1994 | Berchin | 364/487 |
| 5,383,876 A | 1/1995 | Nardella | 606/49 |
| 5,445,374 A * | 8/1995 | Clark, Jr. | 473/191 |
| 5,450,845 A | 9/1995 | Axelgaard | |
| 5,474,558 A | 12/1995 | Neubardt | 606/79 |
| 5,480,440 A | 1/1996 | Kambin | |
| 5,482,038 A | 1/1996 | Ruff | 128/642 |
| 5,484,437 A | 1/1996 | Michelson | |
| 5,540,235 A * | 7/1996 | Wilson | 600/554 |
| 5,549,656 A | 8/1996 | Reiss | 607/48 |
| 5,560,372 A | 10/1996 | Cory | 128/741 |
| 5,566,678 A | 10/1996 | Cadwell | 128/731 |
| 5,579,781 A | 12/1996 | Cooke | 128/733 |
| 5,593,429 A | 1/1997 | Ruff | 607/116 |
| 5,599,279 A | 2/1997 | Slotman et al. | |
| 5,630,813 A | 5/1997 | Kieturakis | 606/46 |
| 5,667,508 A | 9/1997 | Errico et al. | |
| 5,671,752 A | 9/1997 | Sinderby et al. | 128/733 |
| 5,707,359 A | 1/1998 | Bufalini | 604/104 |
| 5,711,307 A | 1/1998 | Smits | 128/733 |
| 5,728,046 A * | 3/1998 | Mayer et al. | 600/210 |
| 5,741,253 A | 4/1998 | Michelson | |
| 5,759,159 A | 6/1998 | Masreliez | |
| 5,772,661 A | 6/1998 | Michelson | |
| 5,775,331 A | 7/1998 | Raymond et al. | 128/741 |
| 5,776,144 A | 7/1998 | Leysieffer et al. | |
| 5,779,642 A | 7/1998 | Nightengale | 600/461 |
| 5,785,658 A | 7/1998 | Benaron | |
| 5,797,854 A | 8/1998 | Hedgecock | 600/554 |
| 5,814,073 A | 9/1998 | Bonutti | 606/232 |
| 5,830,151 A | 11/1998 | Hadzic et al. | 600/554 |
| 5,851,191 A | 12/1998 | Gozani | 600/554 |
| 5,853,373 A | 12/1998 | Griffith et al. | 600/554 |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | 600/461 |
| 5,888,196 A | 3/1999 | Bonutti | 600/204 |
| 5,902,231 A | 5/1999 | Foley et al. | |
| 5,928,139 A * | 7/1999 | Koros et al. | 600/205 |
| 5,928,158 A | 7/1999 | Aristides | 600/547 |
| 5,976,094 A | 11/1999 | Gozani et al. | 600/483 |
| 6,004,262 A | 12/1999 | Putz et al. | 600/114 |
| 6,027,456 A | 2/2000 | Feler et al. | 600/554 |
| 6,038,469 A | 3/2000 | Karlsson et al. | |
| 6,038,477 A | 3/2000 | Kayyali | 607/72 |
| 6,050,992 A | 4/2000 | Nichols | 606/41 |
| 6,074,343 A * | 6/2000 | Nathanson et al. | 600/214 |
| 6,104,957 A | 8/2000 | Alo et al. | 607/46 |
| 6,104,960 A | 8/2000 | Duysens et al. | |
| 6,120,503 A | 9/2000 | Michelson | |
| 6,132,386 A | 10/2000 | Gozani et al. | 600/554 |
| 6,132,387 A | 10/2000 | Gozani et al. | 600/554 |
| 6,135,965 A | 10/2000 | Tumer et al. | 600/476 |
| 6,139,493 A * | 10/2000 | Koros et al. | 600/215 |
| 6,146,335 A | 11/2000 | Gozani | 600/554 |
| 6,161,047 A | 12/2000 | King et al. | 607/62 |
| 6,181,961 B1 | 1/2001 | Prass | |
| 6,206,826 B1 * | 3/2001 | Mathews et al. | 600/210 |
| 6,224,549 B1 | 5/2001 | Drongelen | 600/300 |
| 6,259,945 B1 | 7/2001 | Epstein et al. | 600/547 |
| 6,266,558 B1 | 7/2001 | Gozani et al. | 600/547 |
| 6,273,905 B1 | 8/2001 | Streeter | |
| 6,292,701 B1 | 9/2001 | Prass et al. | 607/116 |
| 6,306,100 B1 * | 10/2001 | Prass | 600/554 |
| 6,312,392 B1 | 11/2001 | Herzon | 600/554 |
| 6,325,764 B1 * | 12/2001 | Griffith et al. | 600/554 |
| 6,334,068 B1 | 12/2001 | Hacker | |
| 6,425,859 B1 | 7/2002 | Foley et al. | |
| 6,425,901 B1 | 7/2002 | Zhu et al. | |
| 6,451,015 B1 | 9/2002 | Rittman, III et al. | |
| 6,466,817 B1 | 10/2002 | Kaula et al. | 600/546 |
| 6,500,128 B2 | 12/2002 | Marino | 600/554 |
| 6,564,078 B1 | 5/2003 | Marino et al. | 600/373 |
| 6,579,244 B2 | 6/2003 | Goodwin | |
| 6,719,692 B2 | 4/2004 | Kleffner et al. | |
| 6,760,616 B2 | 7/2004 | Hoey et al. | |
| 6,796,985 B2 | 9/2004 | Bolger et al. | |
| 6,819,956 B2 | 11/2004 | DiLorenzo | |
| 6,849,047 B2 | 2/2005 | Goodwin | |
| 6,855,105 B2 | 2/2005 | Jackson, III et al. | |
| 6,926,728 B2 | 8/2005 | Zucherman et al. | |
| 6,929,606 B2 | 8/2005 | Ritland | |
| 7,050,848 B2 | 5/2006 | Hoey et al. | |
| 7,079,883 B2 | 7/2006 | Marino et al. | |
| 7,089,059 B1 | 8/2006 | Pless | |
| 7,177,677 B2 | 2/2007 | Kaula et al. | |
| 7,207,949 B2 * | 4/2007 | Miles et al. | 600/554 |
| 2001/0039949 A1 | 11/2001 | Loubser | |
| 2001/0056280 A1 | 12/2001 | Underwood et al. | |
| 2002/0007129 A1 | 1/2002 | Marino | 600/546 |
| 2002/0010392 A1 | 1/2002 | Desai | |
| 2002/0072686 A1 | 6/2002 | Hoey et al. | 600/547 |
| 2002/0161415 A1 * | 10/2002 | Cohen et al. | 607/48 |
| 2002/0193843 A1 | 12/2002 | Hill et al. | |
| 2003/0032966 A1 | 2/2003 | Foley et al. | |

| | | | |
|---|---|---|---|
| 2003/0105503 | A1 | 6/2003 | Marino et al. |
| 2003/0225405 | A1 | 12/2003 | Weiner |
| 2004/0199084 | A1 | 10/2004 | Kelleher |
| 2004/0225228 | A1 | 11/2004 | Ferree |
| 2005/0004593 | A1 | 1/2005 | Simonson |
| 2005/0004623 | A1 | 1/2005 | Miles et al. |
| 2005/0075578 | A1 | 4/2005 | Gharib et al. |
| 2005/0149035 | A1 | 7/2005 | Pimentra et al. |
| 2005/0182454 | A1 | 8/2005 | Gharib et al. |
| 2005/0192575 | A1 | 9/2005 | Pacheco |
| 2006/0025703 | A1 | 2/2006 | Miles et al. |
| 2006/0069315 | A1 | 3/2006 | Miles et al. |
| 2006/0224078 | A1 | 10/2006 | Hoey et al. |
| 2007/0016097 | A1 | 1/2007 | Farquhar et al. |
| 2007/0293782 | A1 | 12/2007 | Marino et al. |

FOREIGN PATENT DOCUMENTS

| | | |
|---|---|---|
| EP | 0972538 A2 | 1/2000 |
| FR | 2795624 | 1/2001 |
| WO | WO-0038574 A1 | 7/2000 |
| WO | WO-0067645 A1 | 11/2000 |
| WO | WO-0137728 A1 | 5/2001 |
| WO | WO-03037170 A3 | 5/2003 |
| WO | WO-2005013805 A3 | 2/2005 |
| WO | WO-2005030318 | 4/2005 |
| WO | WO-2006042241 A2 | 4/2006 |

OTHER PUBLICATIONS

"Nerve Proximity and Status Detection System and Method", *International Search Report*, International Application No. PCT/US01/18606,(Oct. 18, 2001), 6 pages.

"Relative Nerve Movement and Status Detection System and Method", *International Search Report*, International Application No. PCT/US01/18579,(Jan. 15, 2002), 6 pages.

"System and Method for Determining Nerve Proximity, Direction, and Pathology During Surgery", *International Search Report*, International Application No. PCT/US02/22247,(Mar. 27, 2003), 4 pages.

"System and Methods for Determining Nerve Direction to a Surgical Instrument", *International Search Report*, International Application No. PCT/US03/02056,(Aug. 12, 2003), 5 pages.

"Systems and Methods for Performing Percutaneous Pedicle Integrity Assessments", *International Search Report*, International Application No. PCT/US02/35047,(Aug. 11, 2003), 5 pages.

"Systems and Methods for Performing Surgery Procedures and Assessments", *International Search Report*, International Application No. PCT/US02/30617,(Jun. 5, 2003), 4 pages.

Bose, et al., "Neurophysiologic Monitoring of Spinal Nerve Root Function During Instrumented Posterior Lumbar Spine Surgery", *Spine*, 27(13), (2002), pp. 1444-1450.

Calancie, et al., "Stimulus-Evoked EMG Monitoring During Transpedicular Lumbosacral Spine Instrumentation", *Spine*, 19(24), (1994), pp. 2780-2786.

Clements, et al., "Evoked and Spontaneous Electromyography to Evaluate Lumbosacral Pedicle Screw Placement", *Spine*, 21(5), (1996),pp. 600-604.

Ford, et al., "Electrical Characteristics of Peripheral Nerve Stimulators Implications for Nerve Localization", *Regional Anesthesia*, 9, (1984), pp. 73-77.

Glassman, et al., "A Prospective Analysis of Intraoperative Electromyographic Monitoring of Pedicle Screw Placement With Computed Tomographic Scan Confirmation", *Spine* , 20(12), (1995), pp. 1375-1379.

Greenblatt, et al., "Needle Nerve Stimulator-Locator: Nerve Blocks with a New Instrument for Locating Nerves", *Anesthesia & Analgesia*, 41(5), (1962), pp. 599-602.

Holland, N. , "Intraoperative Electromyography During Thoracolumbar Spinal Surgery", *Spine*, 23(17), (1998), pp. 1915-1922.

Lenke, et al., "Triggered Electromyographic Threshold for Accuracy of Pedicle Screw Placement", *Spine*, 20 (14), (1995), 1585-1591.

Maguire, et al., "Evaluation of Intrapedicular Screw Position Using Intraoperative Evoked Electromyography", *Spine*, 20(9), (1995), pp. 1068-1074.

Martin, et al., "Initiation of Erection and Semen Release by Rectal Probe Electrostimulation (RPE)", *The Williams & Wilkins Co.*, (1983), pp. 637-642.

Pither, et al., ""The Use of Peripheral Nerve Stimulators for Regional Anesthesia: Review of Experimental Characteristics, Technique, and Clinical Applications"", *Regional Anesthesia*, (1985), pp. 10:47-53.

Raj, et al., "Infraclavicular Brachial Plexus Block—A New Approach", *Anesthesia and Analgesia*, (52)6, (1973), pp. 897-904.

Raj, et al., "The Use of Peripheral Nerve Stimulators For Regional Anesthesia", *Clinical Issues In Regional Anesthesia*, 1 (4), (1985), pp. 1-6.

Raj, et al., "Use of The nerve Stimulator of Peripheral Blocks", *Regional Anesthesia*, (Apr.-Jun. 1980), pp. 14-21.

Raymond, et al., "The Nerve Seeker: A System for Automated Nerve Localization", *Regional Anesthesia*, 17(3), (1992), pp. 151-162.

Shafik, "Cavernous Nerve Simulation through an Extrapelvic Subpubic Approach: Role in Pencil Erection", *Eur. Urol*, 26, (1994), pp. 98-102.

Toleikis, et al., "The Usefulness of Electrical Stimulation for Assessing Pedicle Screw Replacements", *Journal of Spinal Disorder*, 13(4), (2000), pp. 283-289.

"Brackmann II EMG System", *Medical Electronics*, (1999),4 pages.

"Neurovision SE Nerve Locator/Monitor", *RLN Systems, Inc. Operators Manual*, (1999),22 pages.

"The Brackmann II EMG Monitoring System", *Medical Electronics Co. Operator's Manual Version 1.1*, (1995),50 pages.

"The Nicolet Viking IV", *Nicolet Biomedical Products*, (1999),6 pages.

Anderson, D. G., et al., "Pedicle screws with high electrical resistance: a potential source of error with stimulus-evoked EMG", *Spine*. 27(14):, Department of Orthopaedic Surgery, University of Virginia,(Jul. 15, 2002),1577-1581.

Danesh-Clough, T. , et al., "The use of evoked EMG in detecting misplaced thoracolumbar pedicle screws", *Spine*. 26(12), Orthopaedic Department, Dunedin Hospital,(Jun. 15, 2001),1313-1316.

Darden, B. V., et al., "A comparison of impedance and electromyogram measurements in detecting the presence of pedicle wall breakthrough", *Spine*. 23(2), Charlotte Spine Center, North Carolina,(Jan. 15, 1998),256-262.

Ebraheim, N. A., et al., "Anatomic relations between the lumbar pedicle and the adjacent neural structures", *Spine*. 22(20), Department of Orthopaedic Surgery, Medical College of Ohio,(Oct. 15, 1997),2338-2341.

Haig, "Point of view", *Spine 27* (24), 2819.

Haig, A. J., et al., "The relation among spinal geometry on MRI, paraspinal electromyographic abnormalities, and age in persons referred for electrodiagnostic testing of low back symptoms", *Spine*. 27(17), Department of Physical Medicine and Rehabilitation, University of Michigan,(Sep. 1, 2002),1918-1925.

Holland, N. R., et al. "Higher electrical stimulus intensities are required to activate chronically compressed nerve roots. Implications for intraoperative electromyographic pedicle screw testing", *Spine*. 23(2), Department of Neurology, Johns Hopkins University School of Medicine,(Jan. 15, 1998),224-227.

Minahan, R. E., et al., "The effect of neuromuscular blockade on pedicle screw stimulation thresholds", *Spine*. 25(19), Department of Neurology, Johns Hopkins University, School of Medicine,(Oct. 1, 2000),2526-2530.

"Brackmann II EMG System", *Medical Electronics*, (1999), 4 pages.

"Neurovision SE Nerve Locator/Monitor", *RLN Systems, Inc. Operators Manual*, (1999), 22 pages.

"The Brackmann II EMG Monitoring System", *Medical Electronics Co. Operator's Manual Version 1.1*, (1995), 50 pages.

"The Nicolet Viking IV", *Nicolet Biomedical Products*, (1999), 6 pages.

Danesh-Clough, T., "The use of evoked EMG in detecting misplaced thoracolumbar pedicle screws", *Spine*. 26(12), Orthopaedic Department, Dunedin Hospital, (Jun. 15, 2001), 1313-1316.

Ebraheim, N. A., et al., "Anatomic relations between the lumbar pedicle and the adjacent neural structures", *Spine. 22*(20), Department of Orthopaedic Surgery, Medical College of Ohio, (Oct. 15, 1997), 2338-2341.

Haig, A. J., et al., "The relation among spinal geometry on MRI, paraspinal electromyographic abnormalities, and age in persons referred for electrodiagnostic testing of low back symptoms", *Spine. 27*(17), Department of Physical Medicine and Rehabilitation, University of Michigan, (Sep. 1, 2002), 1918-1925.

Holland, N. R., et al., "Higher electrical stimulus intensities are required to activate chronically compressed nerve roots. Implications for intraoperative electromyographic pedicle screw testing", *Spine. 23*(2), Department of Neurology, Johns Hopkins University School of Medicine, (Jan. 15, 1998), 224-227.

Journee, H. L., et al., "System for Intra-Operative Monitoring of the Cortical Integrity of the Pedicle During Screw Placement in Low-Back Surgery: Design and Clinical Results", *Sensory and neuromuscular diagnostic instrumentation and data analysis, 18th Annual International Conference on Engineering in Medicine and Biology Society,* 1(31), (Oct. 1996), 144-145.

Minahan, R. E., et al., "The effect of neuromuscular blockade on pedicle screw stimulation thresholds", *Spine. 25*(19), Department of Neurology, Johns Hopkins University, School of Medicine, (Oct. 1, 2000), 2526-2530.

Ebraheim, N. A., et al., "Anatomic relations between the lumbar pedicle and the adjacent neural structures", *Spine. 22*(20), Department of Orthopaedic Surgery, Medical College of Ohio, (Oct. 15, 1997), 2338-2341.

Mar. 3, 2005, Office Action in U.S. Appl. No. 10/444,917.
Sep. 5, 2006, Response to Jun. 3, 2006 Office Action in U.S. Appl. No. 10/444,917.
Nov. 28, 2006, Office Action in U.S. Appl. No. 10/444,917.
May 29, 2007, Response to Nov. 28, 2006 Office Action in U.S. Appl. No. 10/444,917.
Dec. 17, 2007, Office Action in U.S. Appl. No. 10/444,917.
Sep. 13, 2006, Office Action in U.S. Appl. No. 10/682,568.
Jan. 16, 2007, Response to Sep. 13, 2006 Office Action in U.S. Appl. No. 10/682,568.
Apr. 19, 2007, Office Action in U.S. Appl. No. 10/682,568.
U.S. Appl. No. 10/444,917, filed May 22, 2003, Bertagnoli, R., et al.
U.S. Appl. No. 10/682,568, filed Oct. 8, 2003, Miles, P., et al.
U.S. Appl. No. 10/789,797, filed Feb. 27, 2004, Miles, P., et al.
Oct. 19, 2007, Response to Apr. 19, 2006 Office Action in U.S. Appl. No. 10/682,568.
Jan. 8, 2008 Office Action in U.S. Appl. No. 10/682,568.
Jun. 16, 2006, Office Action in U.S. Appl. No. 10/789,797.
Dec. 28, 2007, Response to Jun. 16, 2006 Office Action in U.S. Appl. No. 10/789,797.
Jul. 6, 2006, Office Action in U.S. Patent 7207949.
Nov. 27, 2006, Response to Jul. 6, 2006 Office Action in U.S. Patent 7207949.

* cited by examiner

SURGICAL ACCESS SYSTEM AND RELATED METHODS

CROSS-REFERENCES TO RELATED APPLICATIONS

The present application is an International Patent Application of and claims the benefit of priority from commonly owned and co-pending U.S. Provisional Patent Application Ser. Nos. 60/392,214 (filed Jun. 26, 2002), the entire contents of which is hereby expressly incorporated by reference into this disclosure as if set forth fully herein. The present application also incorporates by reference the following co-pending and co-assigned patent applications in their entireties: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003.

BACKGROUND

I. Field

The present invention relates generally to systems and methods for performing surgical procedures and, more particularly, for accessing a surgical target site in order to perform surgical procedures.

II. Description of Related Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY

The present invention accomplishes this goal by providing a novel access system and related methods which involve: (1) distracting the tissue between the patient's skin and the surgical target site to create an area of distraction (otherwise referred to herein as a "distraction corridor"); (2) retracting the distraction corridor to establish and maintain an operative corridor; and/or (3) detecting the existence of (and optionally the distance and/or direction to) neural structures before, during and after the establishment of the operative corridor through (or near) any of a variety of tissues having such neural structures which, if contacted or impinged, may otherwise result in neural impairment for the patient.

As used herein, "distraction" or "distracting" is defined as the act of creating a corridor (extending to a location at or near the surgical target site) having a certain cross-sectional area and shape ("distraction corridor"), and "retraction" or "retracting" is defined as the act of creating an operative corridor by increasing the cross-sectional area of the distraction corridor (and/or modifying its shape) with at least one retractor blade and thereafter maintaining that increased cross-sectional area and/or modified shape such that surgical instruments can be passed through operative corridor to the surgical target site. It is expressly noted that, although described herein largely in terms of use in spinal surgery, the access system of the present invention is suitable for use in any number of additional surgical procedures, including those wherein tissue having significant neural structures must be passed through (or near) in order to establish an operative corridor.

According to one aspect, the present invention provides a surgical access system having an initial tissue distraction assembly and a pivot linkage assembly forming part of a secondary distraction assembly and a retraction assembly. The secondary distraction assembly includes first and second distraction arms forming part of the pivot linkage assembly, first and second speculum blades extending through receiving passageways formed within the first and second distraction arms, and a handle assembly forming part of the pivot linkage. As will be described below, the distraction arms may be advanced over the initial distraction assembly such that the speculum blades are passed into the tissue to be secondarily distracted. Thereafter, the handle assembly may be activated to perform the necessary distraction. That is, the handle assembly can be manipulated by a user to move the first and second distraction arms away from one another, which will at the same time move the distal ends of the speculum blades to create a full distraction corridor.

After the secondary distraction, a pair of retractors blades may be introduced into the distraction corridor and positioned to create an operative corridor to the surgical target site. In a preferred embodiment, retractor blade is introduced first and positioned such that its distal end is generally located towards the posterior region of the spinal target site, which forms a useful barrier to prevent any exiting nerve roots 30 from entering the surgical target site, as well as to prevent any surgical instruments from passing outside the surgical target site and into contact with the exiting nerve roots 30 or other sensitive tissue. The retractor blade may thereafter be introduced and moved in a generally anterior direction away from the retractor blade, effectively creating the operative corridor. The retractor blades may be locked in relation to the pivot linkage assembly in any number of suitable fashions, including but not limited to the use of the nut-bolt assemblies well known in the art. To lock the retractor blades in relation to the surgical target site, optional locking members may be advanced through receiving passageways formed in one or more of the retractor blades such that a distal region of the locking member is brought into a press-fit, secure engagement between the adjacent vertebral bodies to thereby maintain the respective retractor blade in position. With the operative corridor established, any of a variety of surgical instruments, devices, or implants may be passed through and/or manipulated at or near the surgical target site depending upon the given surgical procedure.

According to yet another aspect of the present invention, any number of distraction assemblies and/or retraction assemblies (including but not limited to those described herein) may be equipped to detect the presence of (and optionally the distance and/or direction to) neural structures during the steps tissue distraction and/or retraction. To accomplish this, one or more stimulation electrodes are provided on the various components of the distraction assemblies and/or retraction assemblies, a stimulation source (e.g. voltage or current) is coupled to the stimulation electrodes, a stimulation signal is emitted from the stimulation electrodes as the various components are advanced towards the surgical target site, and the patient is monitored to determine if the stimulation signal causes muscles associated with nerves or neural structures within the tissue to innervate. If the nerves innervate, this indicates that neural structures may be in close proximity to the distraction and/or retraction assemblies.

This monitoring may be accomplished via any number of suitable fashions, including but not limited to observing visual twitches in muscle groups associated with the neural structures likely to found in the tissue, as well as any number of monitoring systems. In either situation (traditional EMG or surgeon-driven EMG monitoring), the access system of the present invention may advantageously be used to traverse tissue that would ordinarily be deemed unsafe or undesirable, thereby broadening the number of manners in which a given surgical target site may be accessed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention is directed at a novel surgical access system and related methods which involve creating a distraction corridor to a surgical target site, thereafter retracting the distraction corridor to establish and maintain an operative corridor to the surgical target site, and optionally detecting the existence of (and optionally the distance and/or direction to) neural structures before, during and/or after the formation of the distraction and/or operative corridors. The steps of distraction followed by retraction are advantageous because they provide the ability to more easily position an operative corridor-establishing device through tissue that is strong, thick or otherwise challenging to traverse in order to access a surgical target site. The various distraction systems of the present invention are advantageous in that they provide an improved manner of atraumatically establishing a distraction corridor prior to the use of the retraction systems of the present invention. The various retractor systems of the present invention are advantageous in that they provide an operative corridor having improved cross-sectional area and shape (including customization thereof) relative to the prior art surgical access systems. Moreover, by optionally equipping the various distraction systems and/or retraction systems with one or more electrodes, an operative corridor may be established through (or near) any of a variety of tissues having such neural structures which, if contacted or impinged, may otherwise result in neural impairment for the patient.

Figure 1:
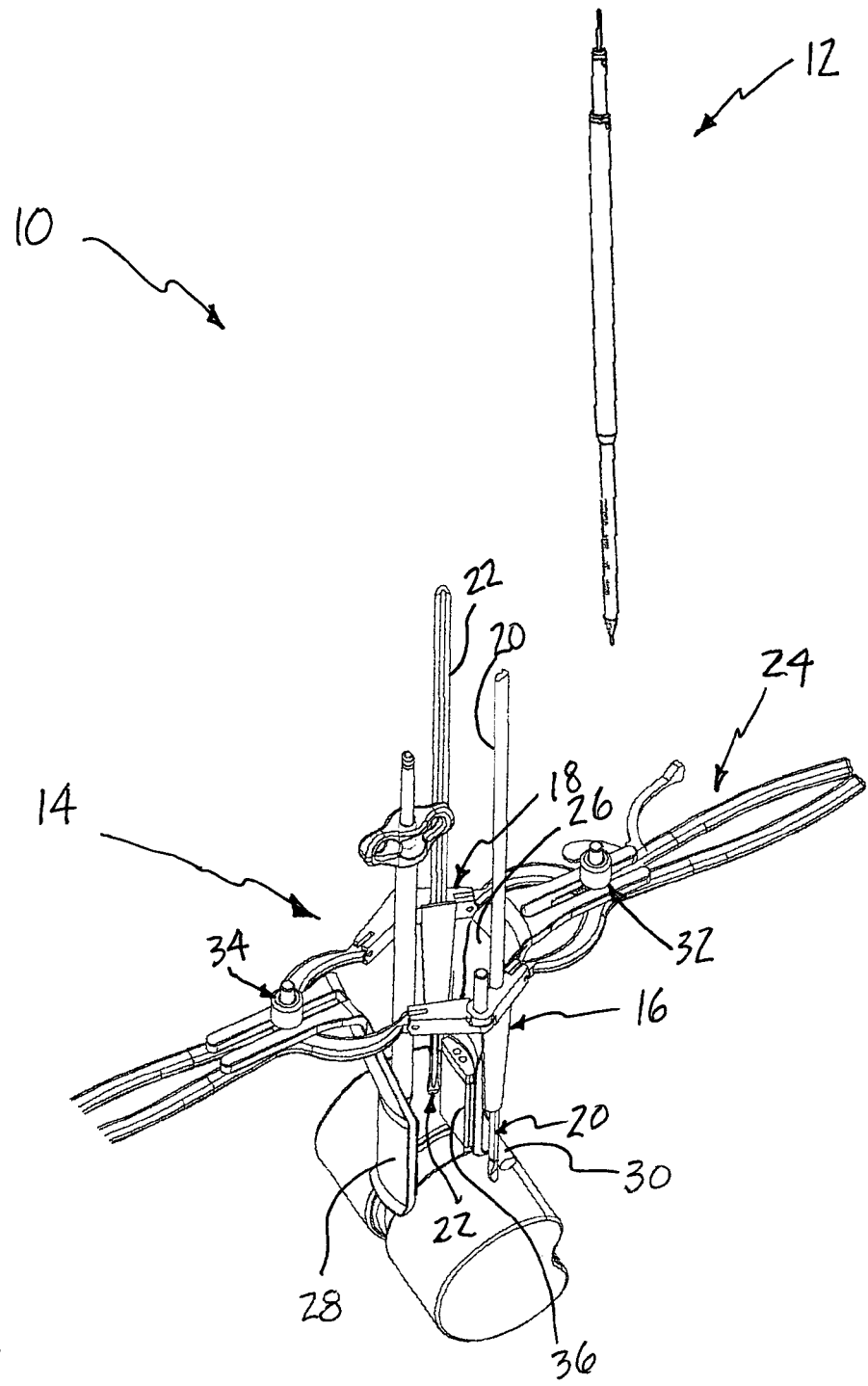
FIG. 1 is a perspective view of a surgical access system according to one aspect of the present invention.

FIG. 1 illustrates a surgical access system 10 according to one aspect of the present invention. The surgical access system 10 includes an initial tissue distraction assembly 12 and a pivot linkage assembly 14 forming part of a secondary distraction assembly and a retraction assembly. The secondary distraction assembly includes first and second distraction arms 16, 18 forming part of the pivot linkage assembly 14, first and second speculum blades 20, 22 extending through receiving passageways formed within the first and second distraction arms 16, 18, and a handle assembly 24 forming part of the pivot linkage 14. As will be described below, the distraction arms 16, 18 may be advanced over the initial distraction assembly 12 such that the speculum blades 20, 22 are passed into the tissue to be secondarily distracted. Thereafter, the handle assembly 24 may be activated to perform the necessary distraction. That is, the handle assembly 24 can be manipulated by a user to move the first and second distraction arms 16, 18 away from one another, which will at the same time move the distal ends of the speculum blades 20, 22 to create a full distraction corridor.

After the secondary distraction, a pair of retractors blades 26, 28 may be introduced into the distraction corridor and positioned to create an operative corridor to the surgical target site. In a preferred embodiment, retractor blade 26 is introduced first and positioned such that its distal end is generally located towards the posterior region of the spinal target site, which forms a useful barrier to prevent any exiting nerve roots 30 from entering the surgical target site, as well as to prevent any surgical instruments from passing outside the surgical target site and into contact with the exiting nerve roots 30 or other sensitive tissue. The retractor blade 28 may thereafter be introduced and moved in a generally anterior direction away from the retractor blade 26, effectively creating the operative corridor. The retractor blades 26, 28 may be locked in relation to the pivot linkage assembly 14 in any number of suitable fashions, including but not limited to the use of the nut-bolt assemblies 32, 34 well known in the art. To lock the retractor blades 26, 28 in relation to the surgical target site, optional locking members 36 may be advanced through receiving passageways formed in one or more of the retractor blades 26, 28 such that a distal region of the locking member 36 is brought into a press-fit, secure engagement between the adjacent vertebral bodies to thereby maintain the respective retractor blade 26, 28 in position. With the operative corridor established, any of a variety of surgical instruments, devices, or implants may be passed through and/or manipulated at or near the surgical target site depending upon the given surgical procedure.

Distraction

Figure 2:
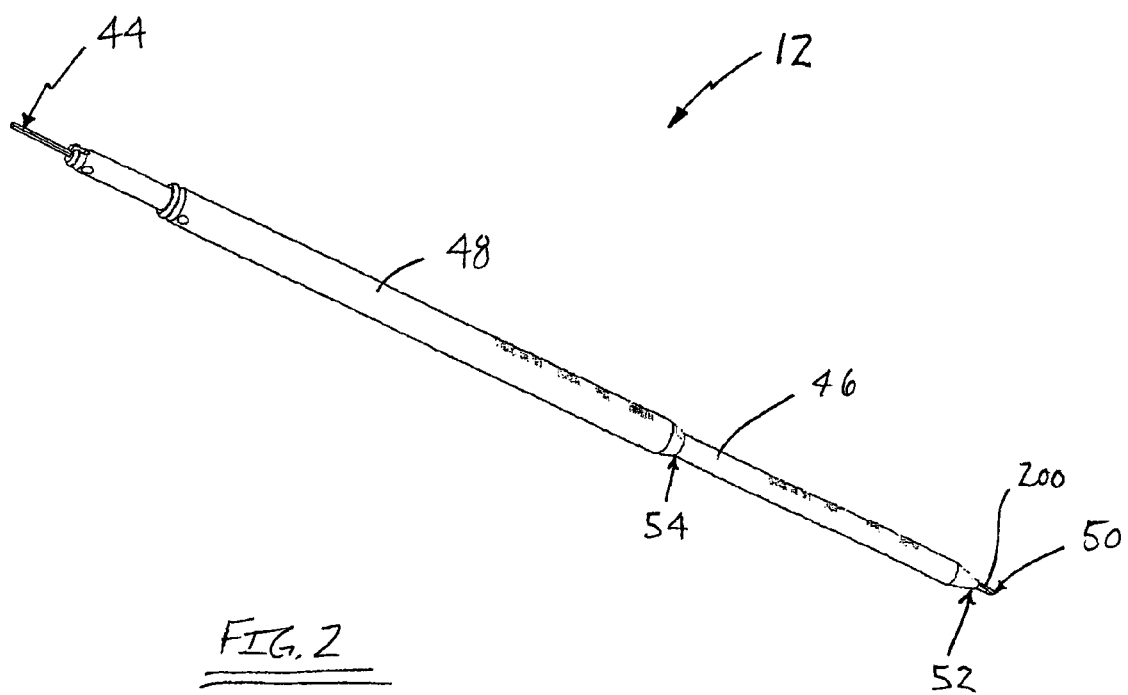
FIG. 2 is a perspective view of an initial tissue distraction assembly forming part of a surgical access system according to the present invention.

FIG. 2 illustrates the initial tissue distraction assembly 12, which is designed to perform an initial distraction of tissue from the skin of the patient down to or near the surgical target site. The initial tissue distraction assembly 12 may be constructed from any number of materials suitable for medical applications, including but not limited to plastics, metals, ceramics or any combination thereof. Depending on the construction, some or all of the tissue distraction assembly 12 may be disposable (i.e. single use) and/or reusable (i.e. multi-use).

The initial tissue distraction assembly 12 may include any number of components capable of performing the necessary initial distraction. By way of example, with combined reference to FIGS. 2-4, this may be accomplished by providing the initial distraction assembly 12 as including a K-wire 44 and one or more dilators 46, 48. The K-wire 44 is preferably constructed having generally narrow diameter (such as, by way of example only, 1.5 mm) and sufficient rigidity and strength such that it can pierce the skin of the patient and be advanced through the intervening tissue to reach the surgical target site. The K-wire 44 also preferably includes indicia for determining the distance between a distal end 50 and the skin of the patient. The dilators 46, 48 are inner and outer dilating elements, respectively, capable of being sequentially introduced over the K-wire 44 for the purpose of further distracting the tissue previously distracted by the K-wire 44.

The inner dilator 46 is preferably constructed having an inner diameter approximating the diameter of the K-wire 44 (such as, by way of example only, 1.5 mm), an outer diameter of increased dimension (such as, by way of example only, 6.5 mm), and indicia for determining the distance between a distal end 52 and the skin of the patient. The outer dilator 48 is similarly preferably constructed having an inner diameter approximating the outer diameter of the inner dilator 46 (such as, by way of example only, 6.5 mm), an outer diameter of increased dimension (such as, by way of example only, 9 mm), and indicia for determining the distance between a distal end 54 and the skin of the patient. The respective lengths of the K-wire 44 and dilators 46, 48 may vary depending upon the given surgical target site (that is, the "depth" of the surgical target site within the patient). It will be similarly appreciated that the diameters and dimensions for these elements may also vary depending upon the particular surgical procedure. All such surgically appropriate variations (length, diameter, etc. . . . ) are contemplated as falling within the scope of the present invention. It is further contemplated and within the scope of the present invention that additional dilators of increasing diameters may be employed to sequentially dilate to the point where a bladed retractor or retraction assembly may be employed to thereafter create an operative corridor according to the present invention (without the need for secondary distraction as described below).

Figure 5:
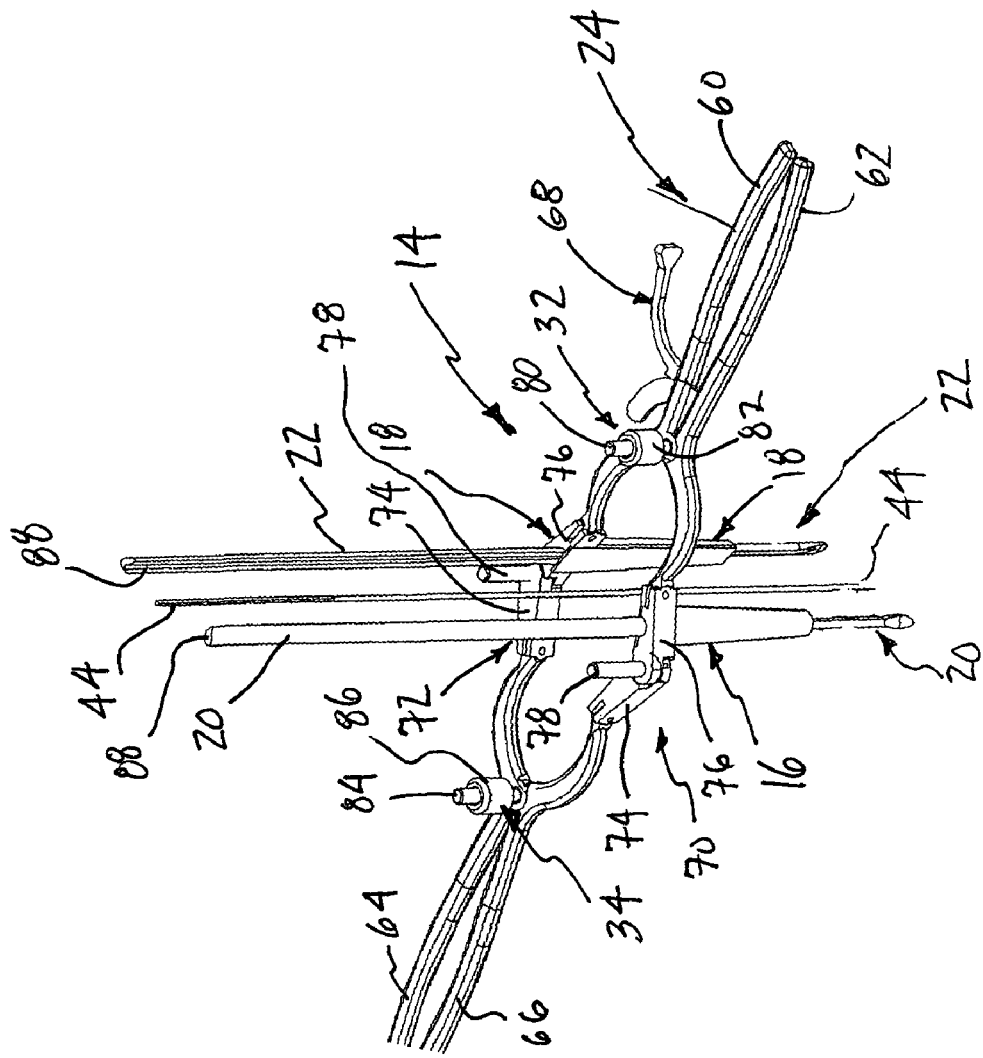
FIG. 5 is a perspective view of a pivot linkage assembly equipped with speculum blades according to the present invention.
Figure 6:
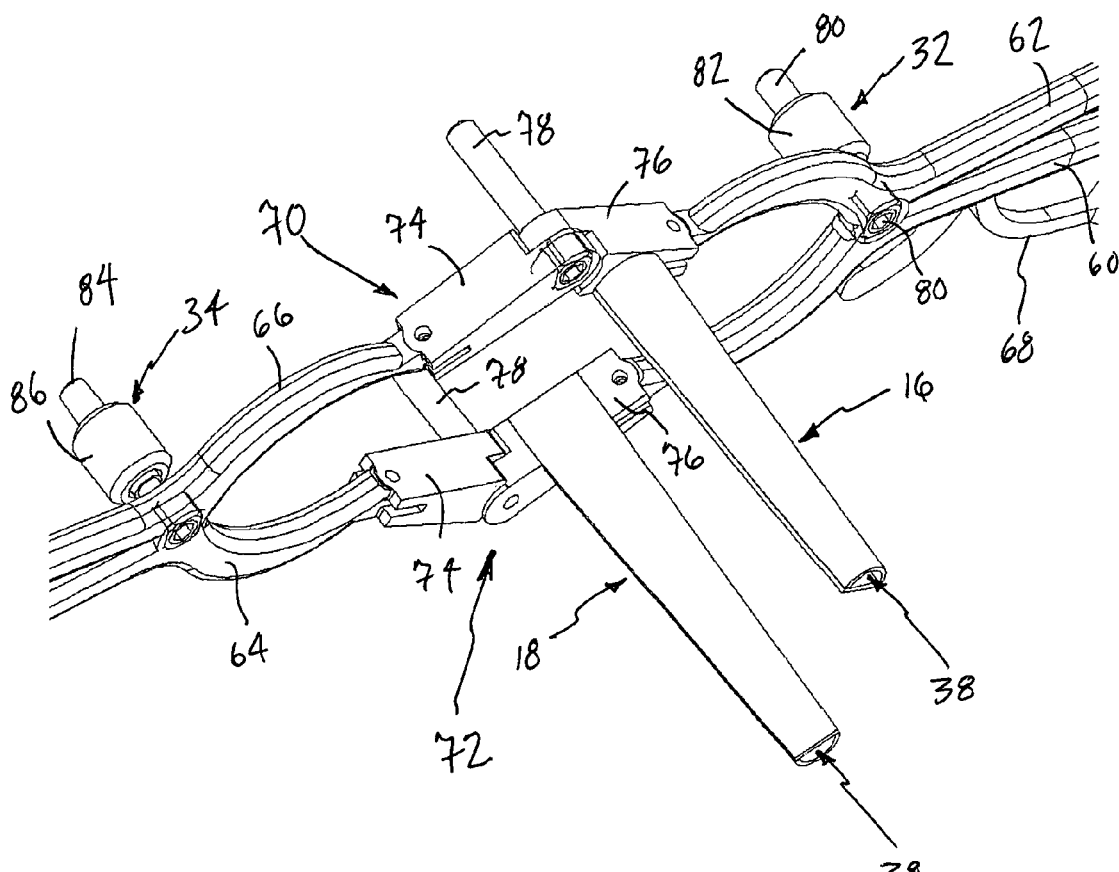
FIG. 6 is a side view of the pivot linkage assembly shown in FIG. 5.
Figure 7:
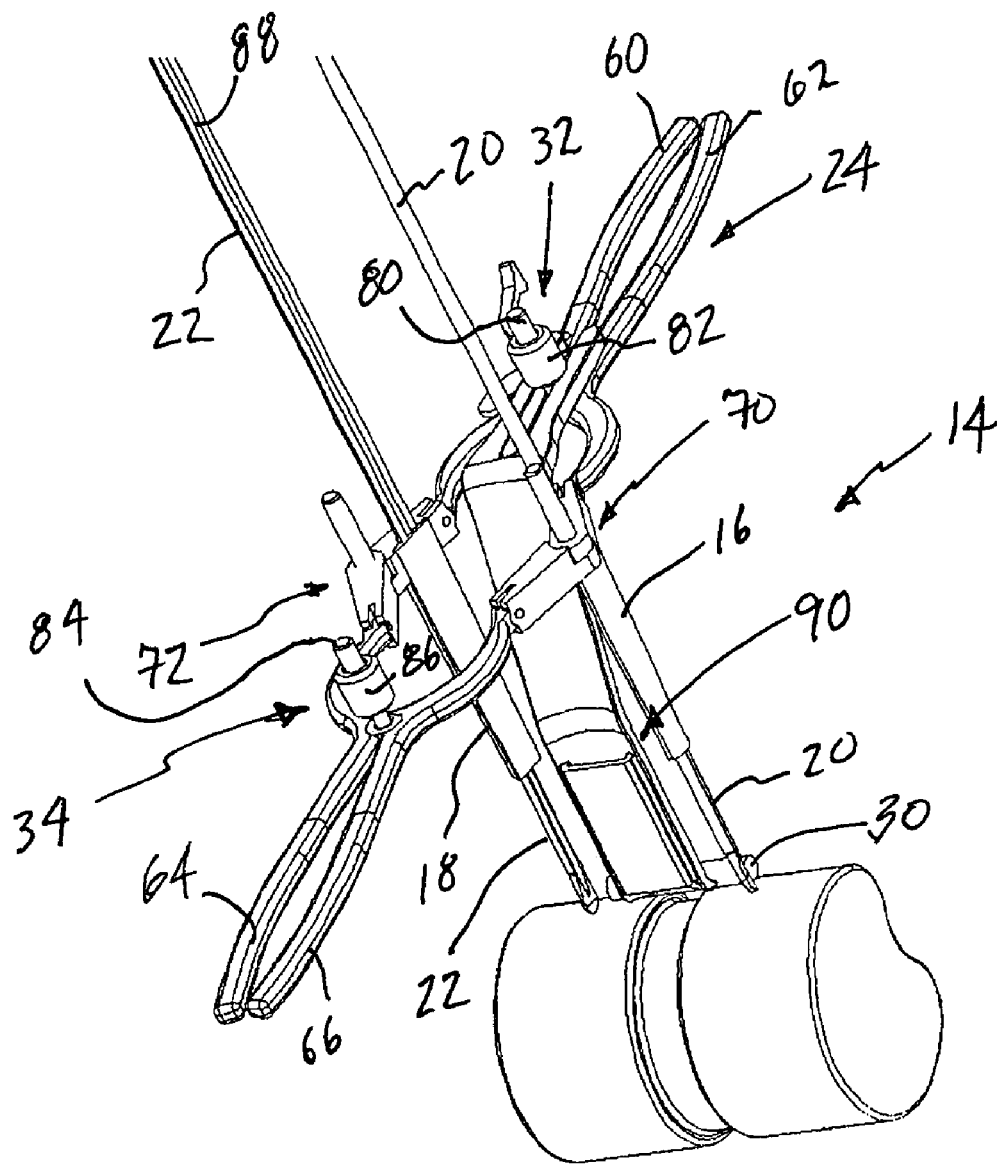
FIGS. 7-8 are perspective views showing the pivot linkage assembly of FIG. 5 in use.
Figure 8:
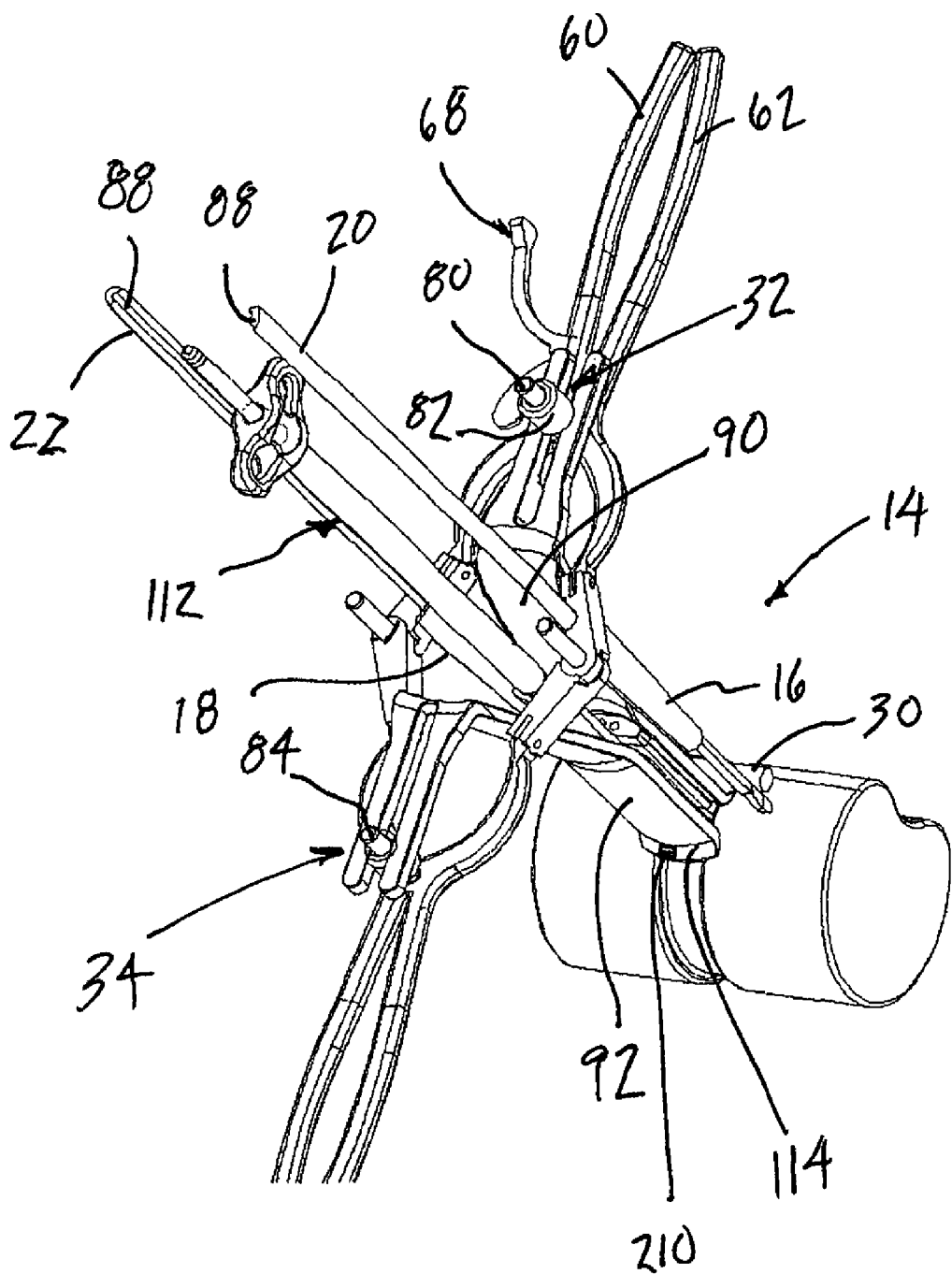
Figure 9:
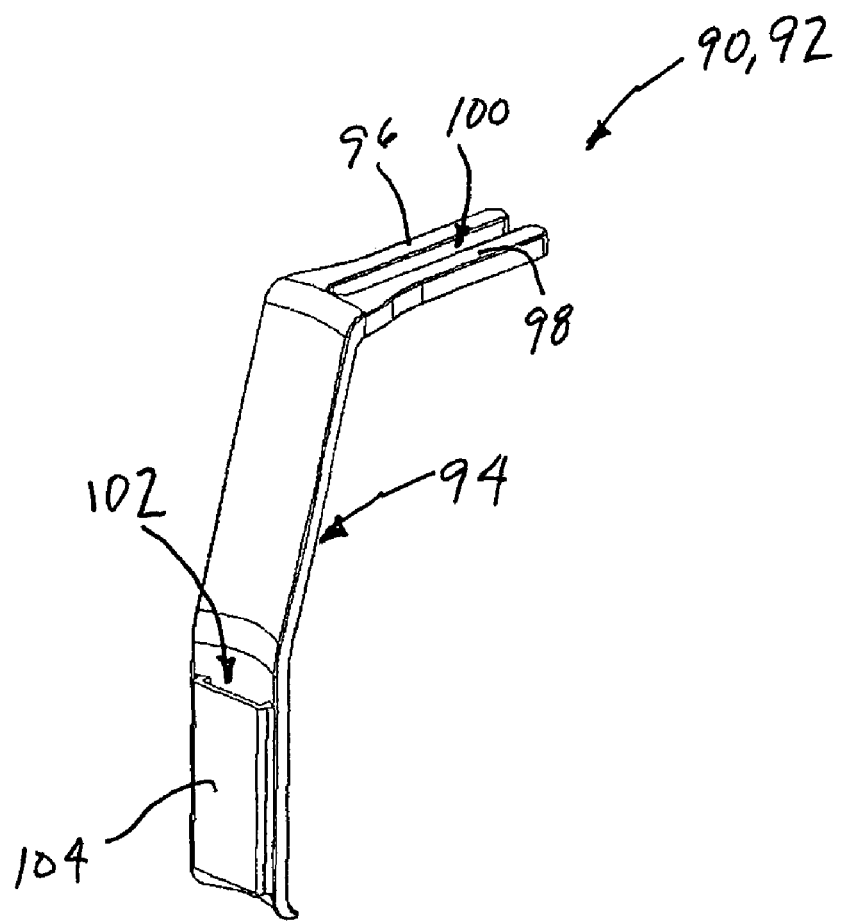
FIGS. 9-10 are perspective views of a retractor blade forming part of a surgical access system according to the present invention.
Figure 10:
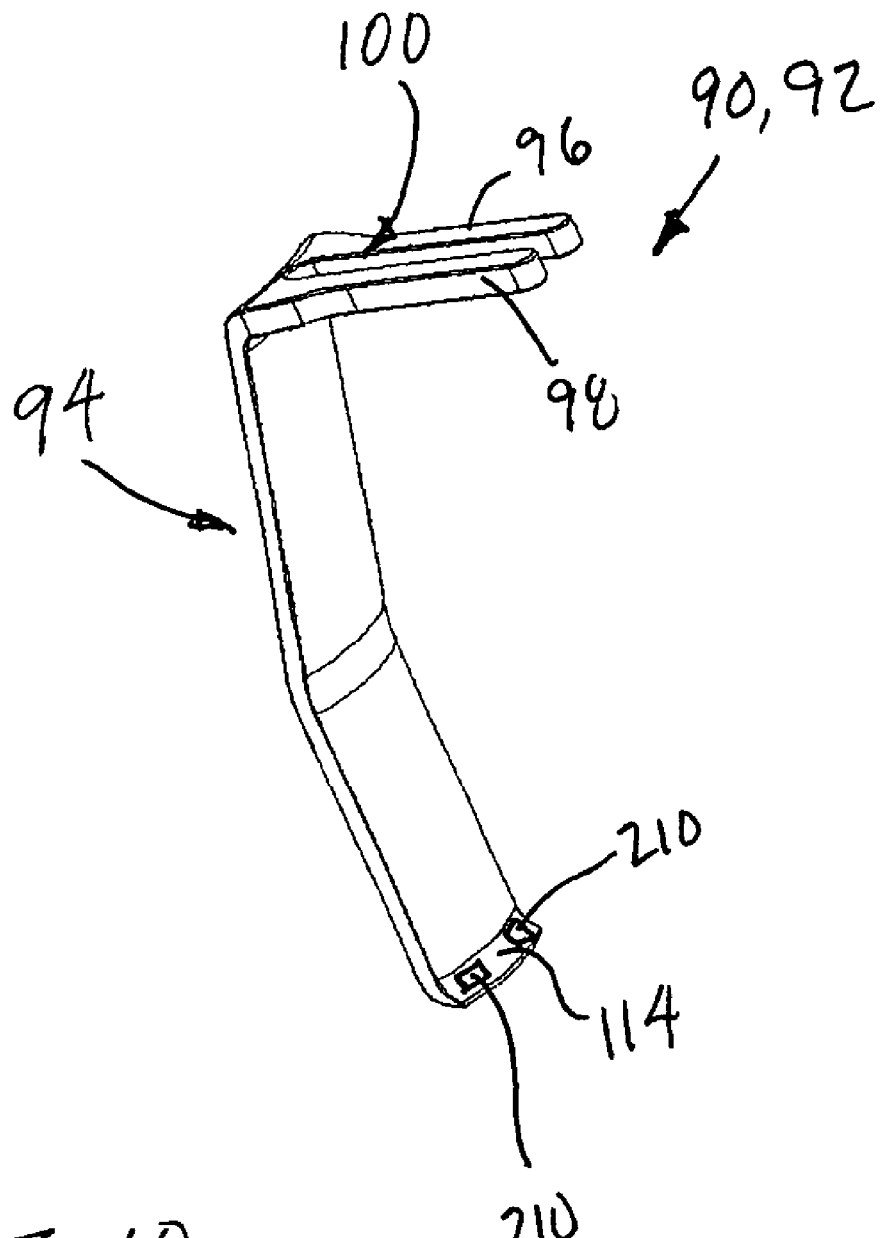

Referring to FIGS. 5-6, the secondary tissue distraction is preferably performed using the pivot linkage assembly 14 in conjunction with the first and second distraction arms 16, 18 and first and second speculum blades 20, 22. The speculum blades 20, 22 extend through receiving passageways 38 (FIG. 6) formed within the first and second distraction arms 16, 18. The handle assembly 24 includes first and second pivot arms 60, 62 disposed on one end of the assembly, and third and fourth pivot arms 64, 66 on the opposite end. First and second pivot arms 60, 62 are pivotably coupled via a rod 80 forming part of the locking assembly 32 (a locking nut 82 forms the remainder of the locking assembly 32). Second and third pivot arms 64, 66 are pivotably coupled via a rod 84 forming part of the locking assembly 34 (a locking nut 86 forms the remainder of the locking assembly 34).

First and second linkage assemblies 70, 72 extend between the distal ends of the pivot arms 60-66, each including a pair of linkages 74, 76 pivotably coupled together via a rod 78. A ratchet member 68 may be used to maintain the first pivot arms 60 relative to the second pivot arm 62 as they are separated during use. As the pivot arms 60, 62 are moved away from one another, the first and second distraction arms 16, 18 (being coupled to or integrally formed with the linkages 76 of first and second linkage assemblies 72, 74) will similarly move away from one another. With the speculum blades 20, 22 disposed within the passageways 38 (FIG. 5), the relative movement of the pivot arms 16, 18 will cause the speculum blades 20, 22 to move apart and thus perform the desired secondary distraction.

The pivot linkage assembly 14 may be constructed from any number of materials suitable for medical applications, including but not limited to plastics, metals, ceramics or any combination thereof. Depending on the construction, some or all of the pivot linkage assembly 14 may be disposable (i.e. single use) and/or reusable (i.e. multi-use).

The speculum blades 20, 22 are generally elongate in nature and include a pair of mating grooves 88 formed along the inwardly facing surfaces of the speculum blades 20, 22 which, when mated together, form a lumen capable of passing over the K-wire 44. In a preferred embodiment, the speculum blades 20, 22 are separable from distraction arms 16, 18 such that the blades 20, 22 can be introduced into the patient and thereafter engaged with the handle assembly 24 to effectuate the secondary distraction. As will be described in greater detail below, this separable construction allows the speculum blades 20, 22 to be introduced down to the surgical target site by passing them through the outer dilator 48 and over with the K-wire 44 (the latter by virtue of the lumen formed by the pair of mating grooves 88 along the inwardly facing surfaces of the speculum blades 20, 22). This is obviously only possible by first removing the inner dilator 46 from within the second dilator 48 while leaving the K-wire 44 in place. Although shown and described herein as being of separable construction, it will be appreciated by those skilled in the art that the speculum blades 20, 22 may be of generally non-separable or fixed construction with the pivot arms 16, 18 of the handle assembly 24.

Retraction

The retraction of the present invention is performed by expanding and/or modifying the distraction corridor to establish and maintain an operative corridor to the surgical target site. As shown in FIGS. 7-10, the pivot linkage 14 is configured to receive (and have coupled thereto) a pair of retractor blades 90, 92 of the type shown in FIGS. 9-10. The retractor blades 90, 92 include a main body element 94 extending downwardly and angularly away from a pair of mounting arms 96, 98. The mounting arms 96, 98 are spaced apart from one another so as to create a channel 100 dimensioned to receive the respective rods 80, 84 of the locking assemblies 32, 34. Once positioned within the channel 100, the retractor blades 90, 92 may be locked in a desired position by tightening the respective nuts 82, 86 of the locking assemblies 32, 34.

Figure 11:
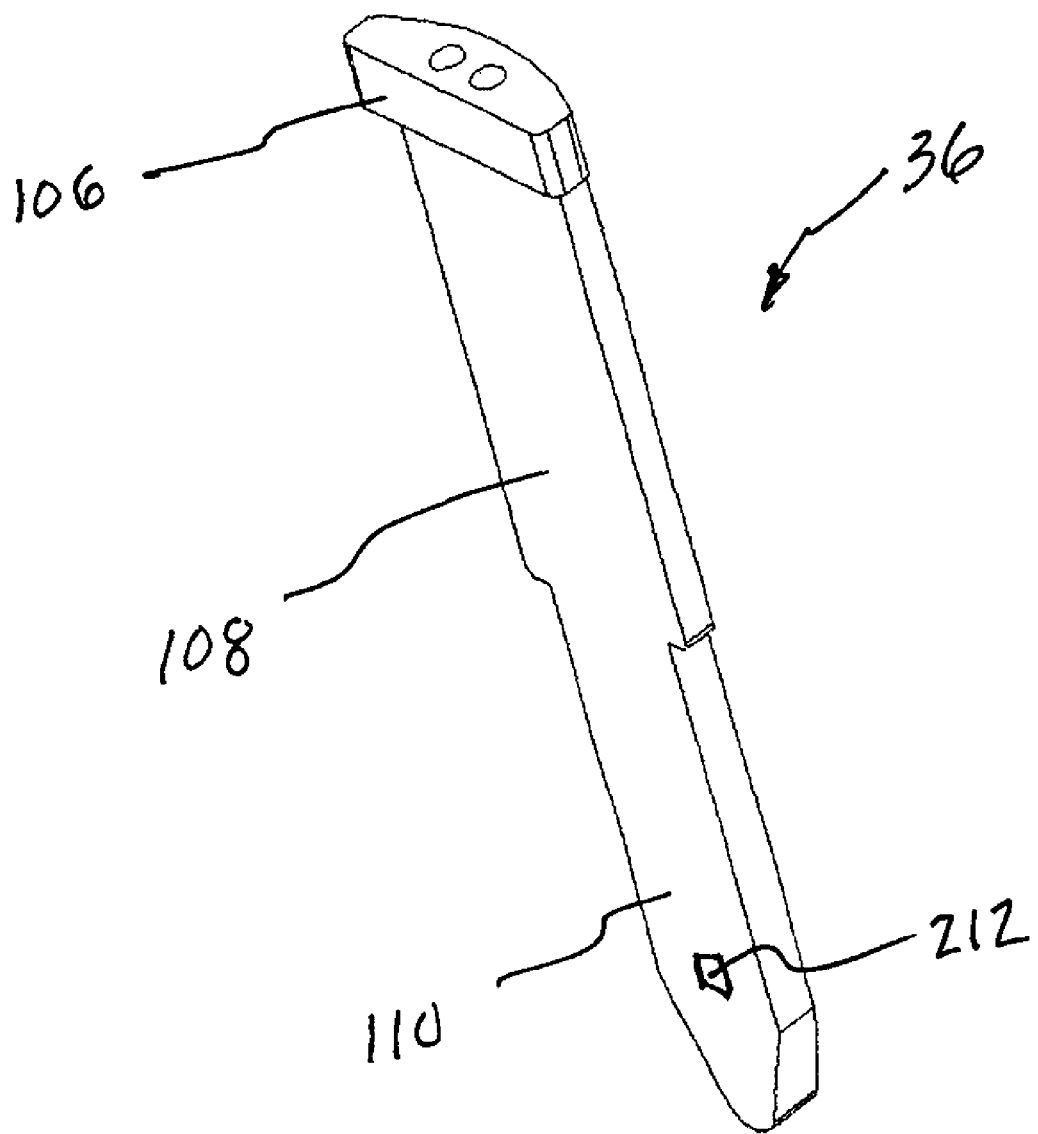
FIG. 11 is a perspective view of a locking member for use with the retractor blade of FIGS. 9-10 according to the present invention.

In a preferred embodiment, one or more of the retractor blades 90, 92 may be equipped with a passageway 102 at or near the distal end of the main body 94, such as by providing a generally planar member 104 along the generally curved distal region of the retractor blade 90, 92. This passageway 102 is dimensioned to receive a locking member 36 of the type shown in FIG. 11. The locking member 36 includes a coupling region 106 for engagement with an introducer tool 112 (FIG. 8), a main body region 108 to be disposed generally within the passageway 102 in use, and a distal region 110 to be introduced into the disc space and engaged between the adjacent vertebral bodies to secure the distal ends of the retractor blades 90, 92 during use. In addition to securing the retractor blades 90, 92 relative to the surgical target site, the distal region 110 also serves to prevent the ingress of unwanted or sensitive biological structures (e.g., nerve roots and/or vasculature) into the surgical target site, as well as prevent instruments from passing outside the surgical target site and contacting surrounding tissues or structures.

The retractor blades 90, 92 may also be optionally provided with at least one guard member 114 extending in a curved fashion (and/or, although not shown, in a generally straight fashion) from the distal end of the retractor blade 90, 92. The guard member 114 may be provided, by way of example, for the purpose of preventing tissue (such as nerve roots in spinal surgery applications) from entering into the operative corridor during surgery and for preventing instruments from extending outside the operative corridor and/or the general vicinity of the surgical target site.

The retractor blades 90, 92 may also be equipped with any number of different mechanisms for transporting or emitting light at or near the surgical target site to aid the surgeon's ability to visualize the surgical target site, instruments and/or implants during the given surgical procedure. For example, one or more strands of fiber optic cable may be coupled to the retractor blades 90, 92 such that light may be delivered from a light source and selectively emitted into the operative corridor and/or the surgical target site. This may be accomplished by constructing the retractor blades 90, 92 of suitable material (such as clear polycarbonate) and configuration such that light may be transmitted generally distally through a light exit region formed along the entire inner periphery of the retractor blade 90, 92 and located in the general vicinity as the distal opening of the passageway 102. This may be performed by providing the retractor blade 90, 92 having light-transmission characteristics (such as with clear polycarbonate construction) and transmitting the light almost entirely within the walls of the retractor blade 90, 92 (such as by frosting or otherwise rendering opaque portions of the exterior and/or interior and coupling the light source thereto such as via a port) until it exits a portion along the interior of the retractor blades 90, 92 to shine at or near the surgical target site.

In one embodiment, a variety of sets of retractor blades 90, 92 may be provided, each having a different length to account for any number of possible surgical target sites. In a further embodiment, each set of retractor blades 90, 92 may be marked or color-coded to aid in indicating to the surgeon the particular length of the blade 90, 92 or the depth of the surgical target site.

The retractor blades 90, 92 and the locking member 36 may be constructed from any number of materials suitable for medical applications, including but not limited to plastics, metals, ceramics or any combination thereof. Depending on the construction, some or all of these devices may be disposable (i.e. single use) and/or reusable (i.e. multi-use).

Any number of suitable mounting units (not shown) may be employed to maintain the pivot linkage assembly 14 in a fixed and rigid fashion relative to the patient. By way of example only, this may be accomplished by providing the mounting unit as a generally U-shaped mounting arm for lockable engagement with the pivot linkage assembly 14, and a coupling mechanism (not shown) extending between the mounting arm and a rigid structure (such as the operating table) for maintaining the U-shaped mounting arm in a fixed and rigid position.

Nerve Surveillance

According to yet another aspect of the present invention, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist. Such monitoring may also be carried out via the surgeon-driven EMG monitoring system shown and described in the following commonly owned and co-pending PCT Applications (collectively "NeuroVision PCT Applications"): PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003. The entire contents of each of the above-enumerated NeuroVision PCT Applications is hereby expressly incorporated by reference into this disclosure as if set forth fully herein.

In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 12:
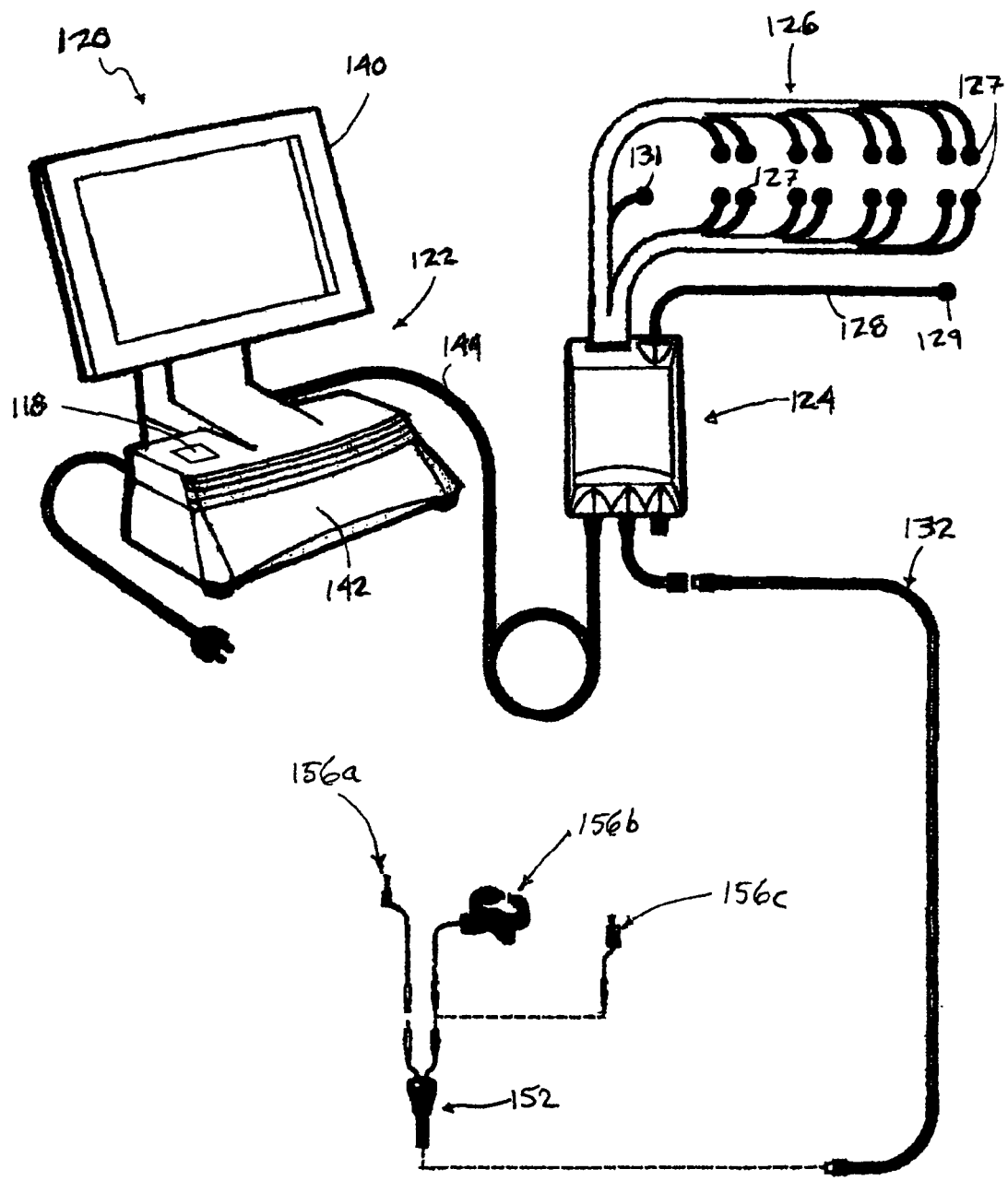
FIG. 12 is a perspective view of an exemplary nerve monitoring system capable of performing nerve monitoring before, during and after the creating of an operative corridor to a surgical target site using the surgical access system in accordance with the present invention.
Figure 13:
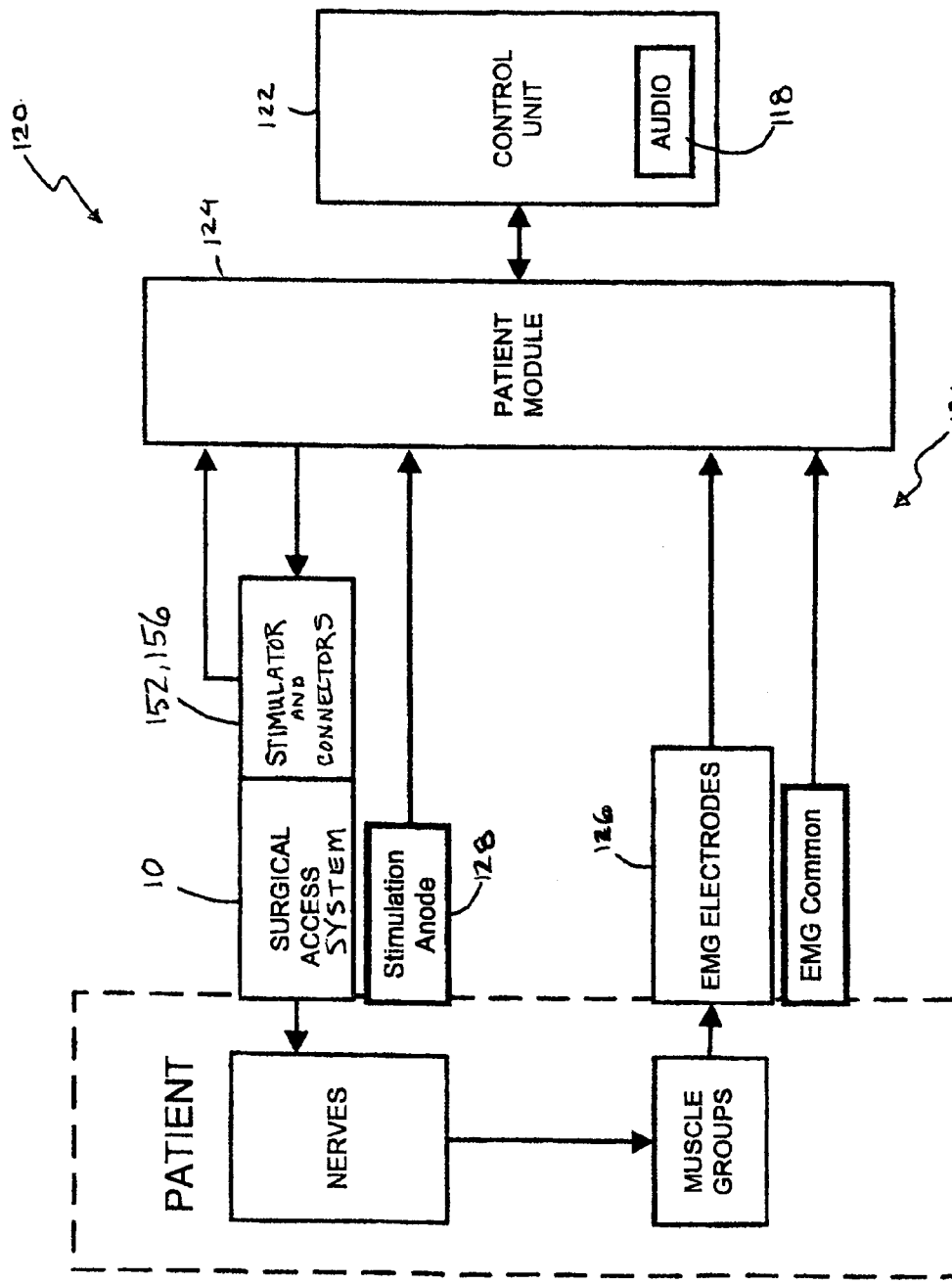
FIG. 13 is a block diagram of the nerve monitoring system shown in FIG. 12.

FIGS. 12-13 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system 10 (FIG. 1). More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrodes on the K-wire 44, the dilators 46, 46, the speculum blades 20, 22, the retractor blades 90, 92, and/or the guard members 114 (collectively "surgical access instruments").

In order to use the monitoring system 120, then, these surgical access instruments must be connected to the connectors 156a, 156b and/or 156c, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the K-wire 44, dilation cannula 46, 48, speculum blades 20, 22, the retractor blades 90, 92, and/or the guard members 114 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

According to one embodiment, the surgical access system detects the presence of (and optionally, the distance and/or direction to) nerves by determining a stimulation current threshold level ("$I_{thresh}$") required to evoke a predetermined neuromuscular response (e.g. an EMG response of 100 uV). $I_{thresh}$ decreases as the degree of electrical communication between a stimulation impulse and a nerve increases. Thus, $I_{thresh}$ is indicative of the degree of communication between a stimulation source and a nerve and may therefore provide the user (by way of example only) with an indication of proximity to the nerve.

In order to quickly determine $I_{thresh}$, the system may employ a threshold-hunting algorithm. According to one embodiment, the threshold-hunting algorithm employs a series of monopolar stimulations to determine the stimulation current threshold for each EMG channel that is in scope. The nerve is stimulated using current pulses with amplitude of $I_{stim}$. The muscle groups respond with an evoked potential that has a peak to peak voltage of $V_{pp}$. $I_{thresh}$ is the minimum $I_{stim}$ that results in a $V_{pp}$ that is greater than a known threshold voltage $V_{thresh}$. The value of $I_{stim}$ is adjusted by a bracketing method as follows. The first bracket comprises two stimulation signals of different $I_{stim}$. By way of example the first bracket may comprise 0.2 mA and 0.3 mA. If the $V_{pp}$ corresponding to both of these stimulation currents is lower than $V_{thresh}$, then the bracket size is doubled to 0.2 mA and 0.4 mA. This exponential doubling of the bracket size continues until the upper end of the bracket results in a $V_{pp}$ that is above $V_{thresh}$. The size of the brackets is then reduced by a bisection method. A current stimulation value at the midpoint of the bracket is used and if this results in a $V_{pp}$ that is above $V_{thresh}$, then the lower half becomes the new bracket. Likewise, if the midpoint $V_{pp}$ is below $V_{thresh}$ then the upper half becomes the new bracket. This bisection method is used until the bracket size has been reduced to a predetermined accuracy. $I_{Thresh}$ may be selected from any value within the final bracket. By way of example, $I_{thresh}$ may be selected as the midpoint of the final bracket.

Figure 14:
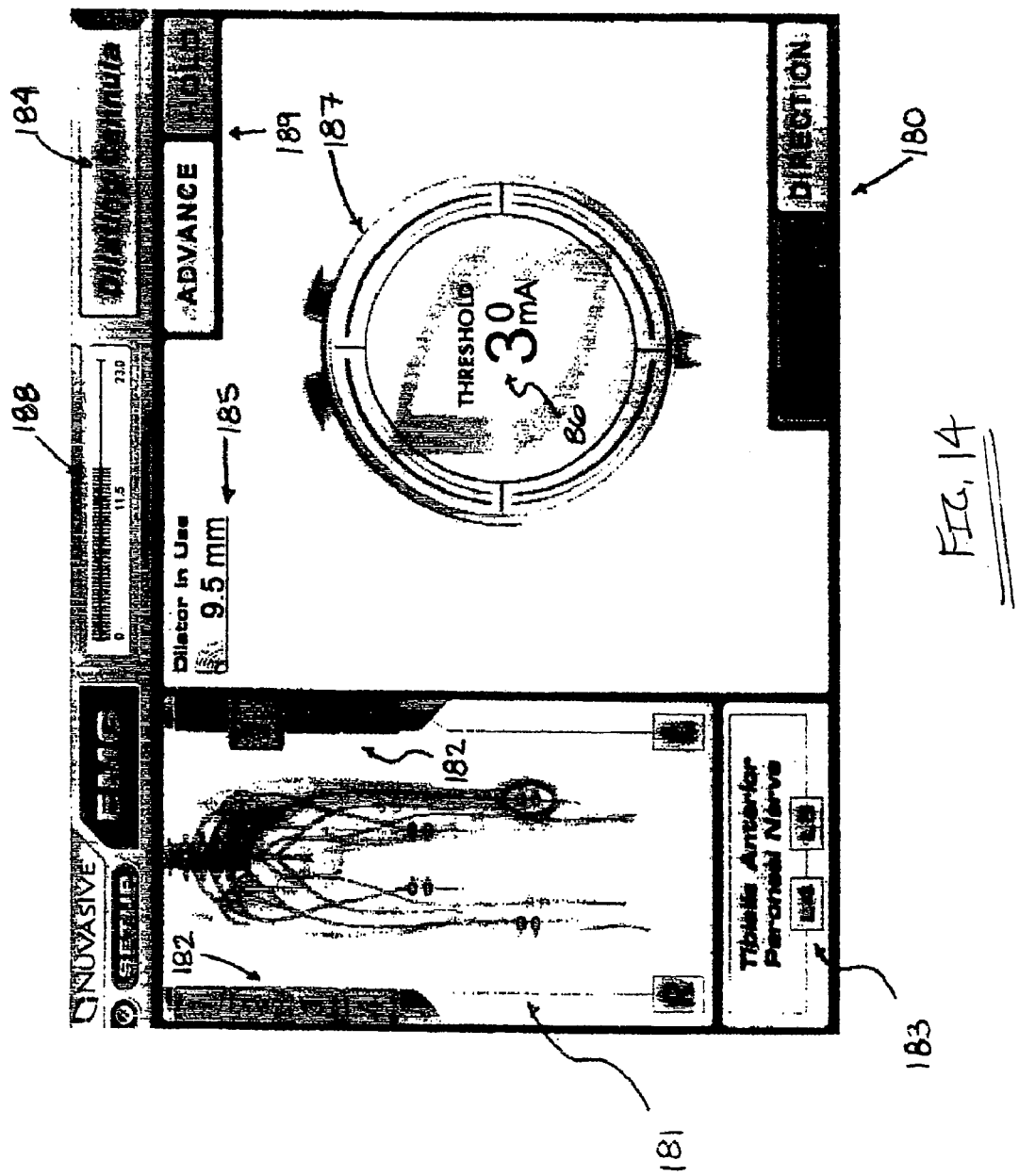
FIGS. 14-15 are screen displays illustrating exemplary features and information communicated to a user during the use of the nerve monitoring system of FIG. 12.
Figure 15:
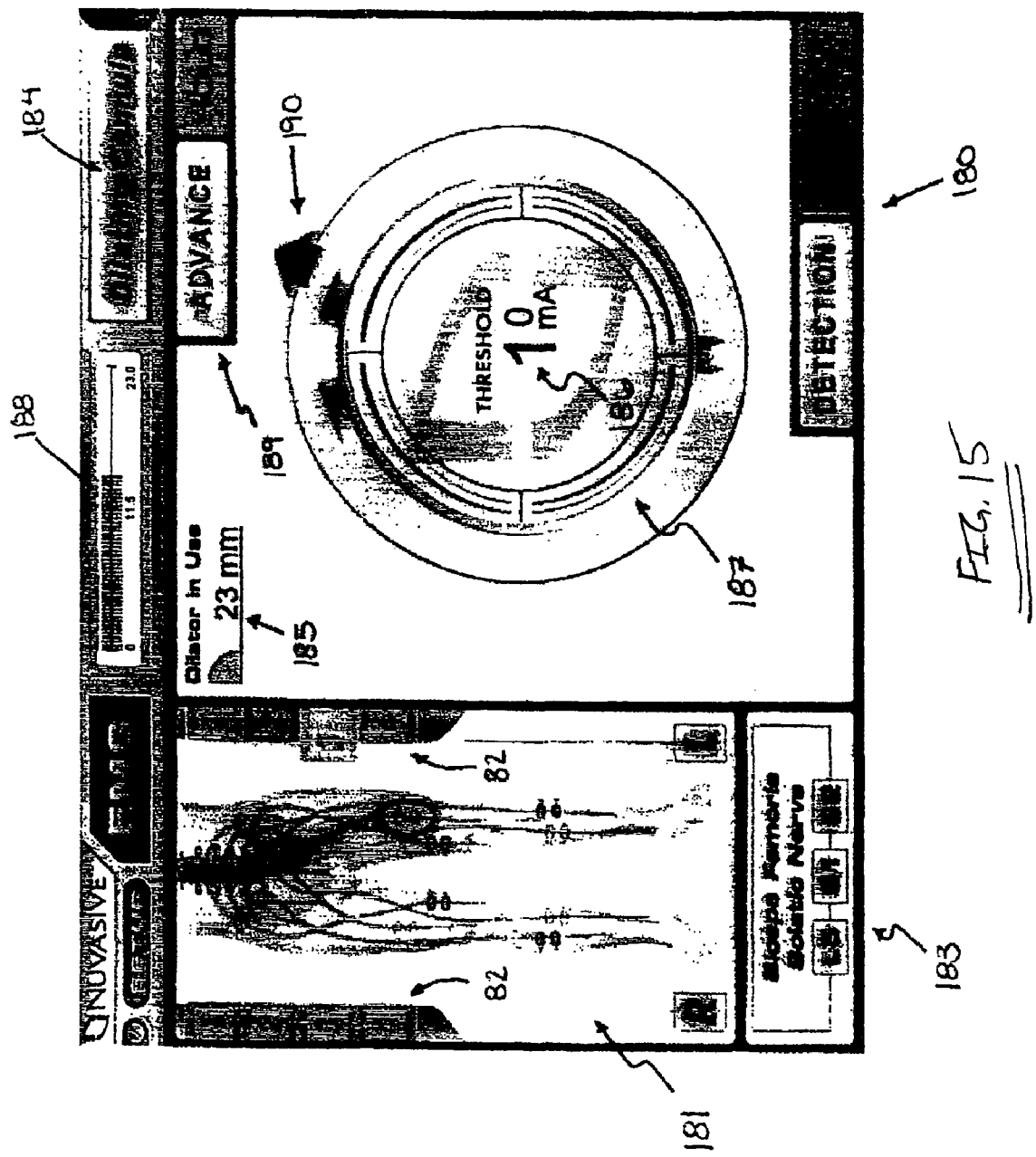

FIGS. 14-15 are exemplary screen displays (to be shown on the display 140) illustrating one embodiment of the nerve direction feature of the monitoring system shown and described with reference to FIGS. 12-13. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 46, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 15) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the initial distraction assembly 12 (i.e. the K-wire 44 and dilators 46, 48), the speculum blades 20, 22 and/or the retractor blades 90, 92 and/or the guard members 114.

Figure 3:
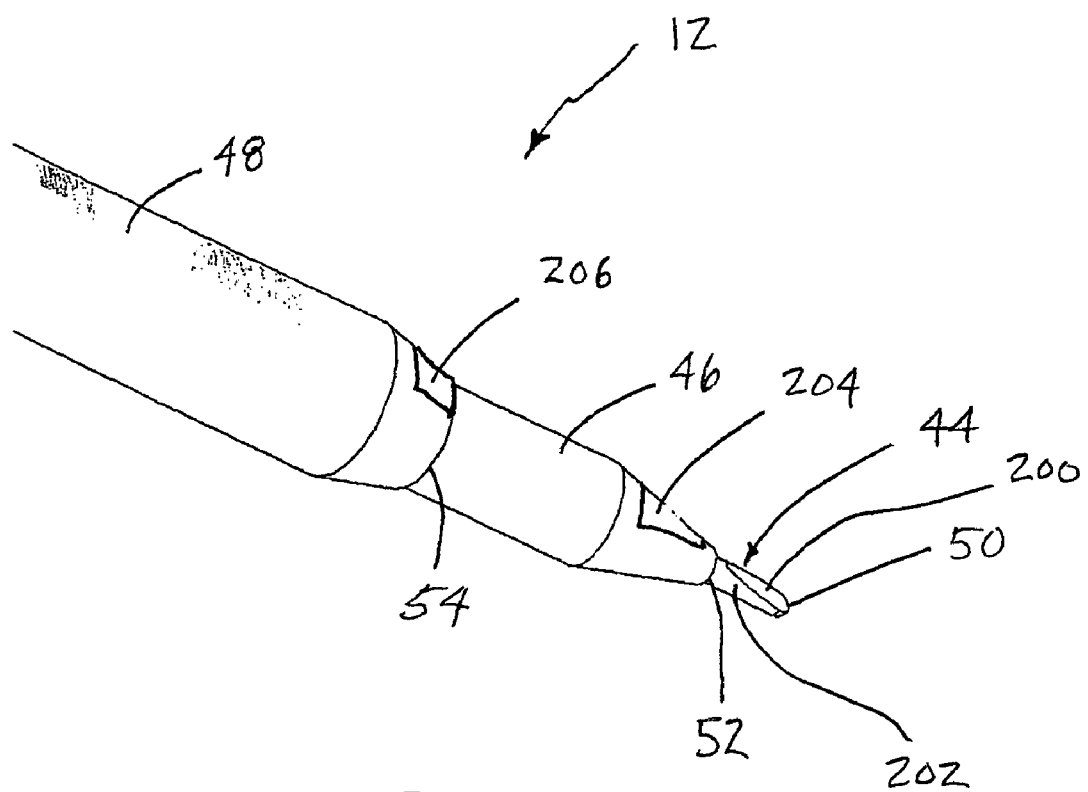
FIGS. 3-4 are exploded views detailing the distal portions of the initial tissue distraction assembly shown in FIG. 2.
Figure 4:
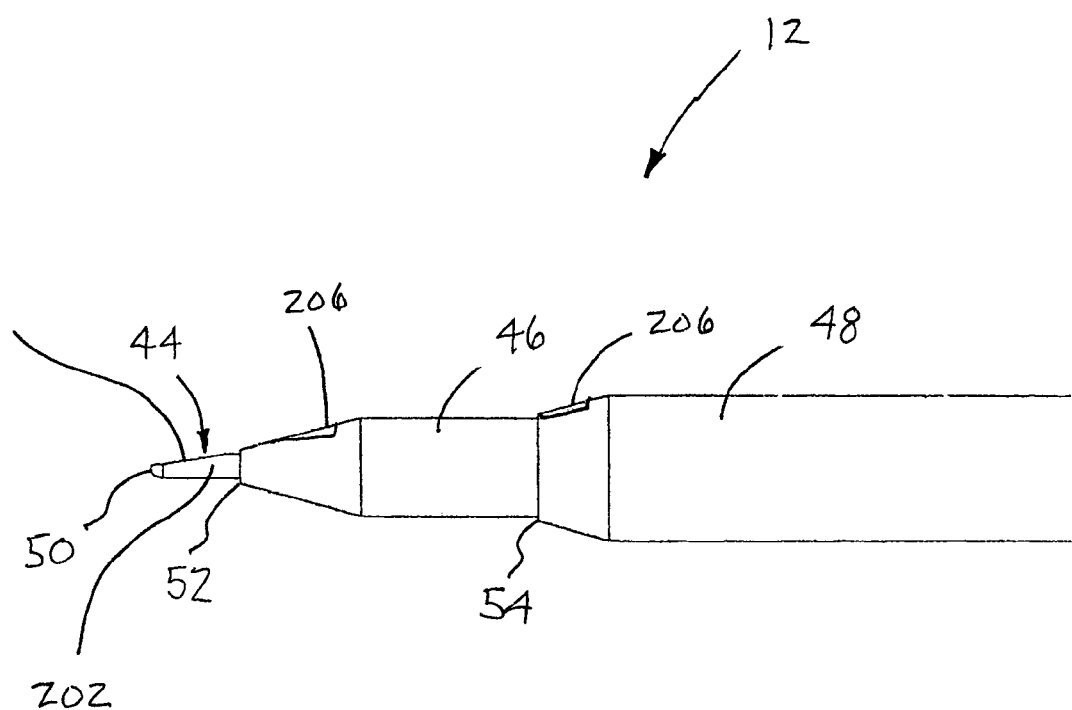

The initial distraction assembly 12 (FIGS. 2-4) may be provided with one or more electrodes for use in providing the neural monitoring capabilities of the present invention. By way of example only, the K-wire 44 may be equipped with a distal electrode 200. This may be accomplished by constructing the K-wire 44 for a conductive material, providing outer layer of insulation 202 extending along the entire length with the exception of an exposure that defines the electrode 200. As best shown in FIGS. 3-4, the electrode 200 has an angled configuration relative to the rest of the K-wire 44 (such as, by way of example only, in the range of between 15 and 75 degrees from the longitudinal axis of the K-wire 44). The angled nature of the electrode 200 is advantageous in that it aids in piercing tissue as the K-wire 44 is advanced towards the surgical target site.

The angled nature of the distal electrode 200 is also important in that it provides the ability to determine the location of nerves or neural structures relative to the K-wire 44 as it is advanced towards or resting at or near the surgical target site. This "directional" capability is achieved by the fact that the angled nature of the electrode 200 causes the electrical stimulation to be projected away from the distal portion of the K-wire 44 in a focused, or directed fashion. The end result is that nerves or neural structures which are generally closer to the side of the K-wire 44 on which the electrode 200 is disposed will have a higher likelihood of firing or being innervated that nerves or neural structures on the opposite side as the electrode 200.

The direction to such nerves or neural structures may thus be determined by physically rotating the K-wire 44 at a particular point within the patient's tissue and monitoring to see if any neural stimulation occurs at a given point within the rotation. Such monitoring can be performed via visual observation, a traditional EMG monitoring, as well as the nerve surveillance system disclosed in the above-referenced NeuroVision PCT Applications. If the signals appear more profound or significant at a given point within the rotation, the surgeon will be able tell where the corresponding nerves or neural structures are, by way of example only, by looking at reference information (such as the indicia) on the exposed part of the K-wire 44 (which reference point is preferably set forth in the exact same orientation as the electrode 200).

Dilators 46, 48 may also be provided with angled electrodes 204, 206, respectively, for the purpose of determining the location of nerves or neural structures relative to the dilators 46, 48 as they are advanced over the K-wire 44 towards or positioned at or near the surgical target site. Due to this similarity in function with the electrode 200 of the K-wire 44, a repeat explanation is not deemed necessary. The dilators 46, 48 may be equipped with the electrodes 204, 206 via any number of suitable methods, including but not limited to providing electrically conductive elements within the walls of the dilators 46, 48, such as by manufacturing the dilators 46, 48 from plastic or similar material capable of injection molding or manufacturing the dilators 46, 48 from aluminum (or similar metallic substance) and providing outer insulation layer with exposed regions (such as by anodizing the exterior of the aluminum dilator).

According to one aspect of the present invention, additional neural monitoring equipment may be employed so as to further prevent inadvertent contact with neural structures. For example, after the initial dilator 46 has been withdrawn in order to subsequently receive the mated speculum blades 20, 22, a confirmation probe (providing a stimulation signal) may be inserted through the outer dilator 48 and to a point at or near the surgical target site. The confirmation probe may thereafter be stimulated for the purpose of double-checking to ensure that no nerves or neural structures are disposed in the tissue near (or have migrated into the vicinity of) the distal end 54 of the outer dilator 48 before introducing the speculum blades 20, 22. By confirming in this fashion, the outer dilator 48 may be removed following the introduction of the speculum blades 20, 22 and the secondary distraction performed (by coupling the handle assembly 24 to the blades 20, 22 and expanding) without fear of inadvertently causing the speculum blades 20, 22 to contact nerves or neural structures.

The secondary distraction of the present invention (FIGS. 5-6) may be provided with one or more electrodes for use in providing the neural monitoring capabilities of the present invention. By way of example only, it may be advantageous to provide one or more electrodes along the speculum blades 20, 22 and/or on the concave region 252 (such as stimulation electrode 208) for the purpose of conducting neural monitoring before, during and/or after the secondary distraction.

The retractor blades 90, 92 of the present invention (FIGS. 7-10) may also be provided with one or more electrodes for use in providing the neural monitoring capabilities of the present invention. By way of example only, it may be advantageous to provide one or more electrodes 210 on the guard members 114 and/or the stimulation electrodes 212 on the locking members 36 (preferably on the side facing away from the surgical target site) for the purpose of conducting neural monitoring before, during and/or after the retractor blades 90, 92 have been positioned at or near the surgical target site.

The surgical access system 10 of the present invention may be sold or distributed to end users in any number of suitable kits or packages (sterile and/or non-sterile) containing some or all of the various components described herein. For example, the pivot linkage assembly 14 may be provided such that the pivot amms 16, 18 and speculum blades 20, 22 are disposable and the retractor blades 90, 92 are re-usable. In a further embodiment, an initial kit may include these materials, including a variety of sets of retractor blades 90, 92 having varying (or "incremental") lengths to account for surgical target sites of varying locations within the patient.

Spine Surgery Example

The surgical access system 10 of the present invention will now be described, by way of example, with reference to the spinal application shown in FIGS. 16-33. It will, of course, be appreciated that the surgical access system and related methods of the present invention may find applicability in any of a variety of surgical and/or medical applications such that the following description relative to the spine is not to be limiting of the overall scope of the present invention. More specifically, while described below employing the nerve monitoring features described above (otherwise referred to as "nerve surveillance") during spinal surgery, it will be appreciated that such nerve surveillance will not be required in all situations, depending upon the particular surgical target site.

FIGS. 16-22 illustrate the method steps involved in using the initial tissue distraction assembly 12 of the present invention. The K-wire 44 is first introduced along a given pathway towards the surgical target site (which, in this case, is an intervertebral disc level of the lumbar spine). Determining the preferred angle of incidence into the surgical target site (as well as the advancement or positioning of any required surgical instruments (such as the surgical access system of the present invention), devices and/or implants) may be facilitated through the use of surgical imaging systems (such as fluoroscopy) as well any number of stereotactic guide systems, including but not limited to those shown and described in co-pending and commonly owned U.S. patent application Ser. No. 09/888,223, filed Jun. 22, 2001 and entitled "Polar Coordinate Surgical Guideframe," the entire contents of which is incorporated by reference as if set forth in its entirety herein.

Figure 16:
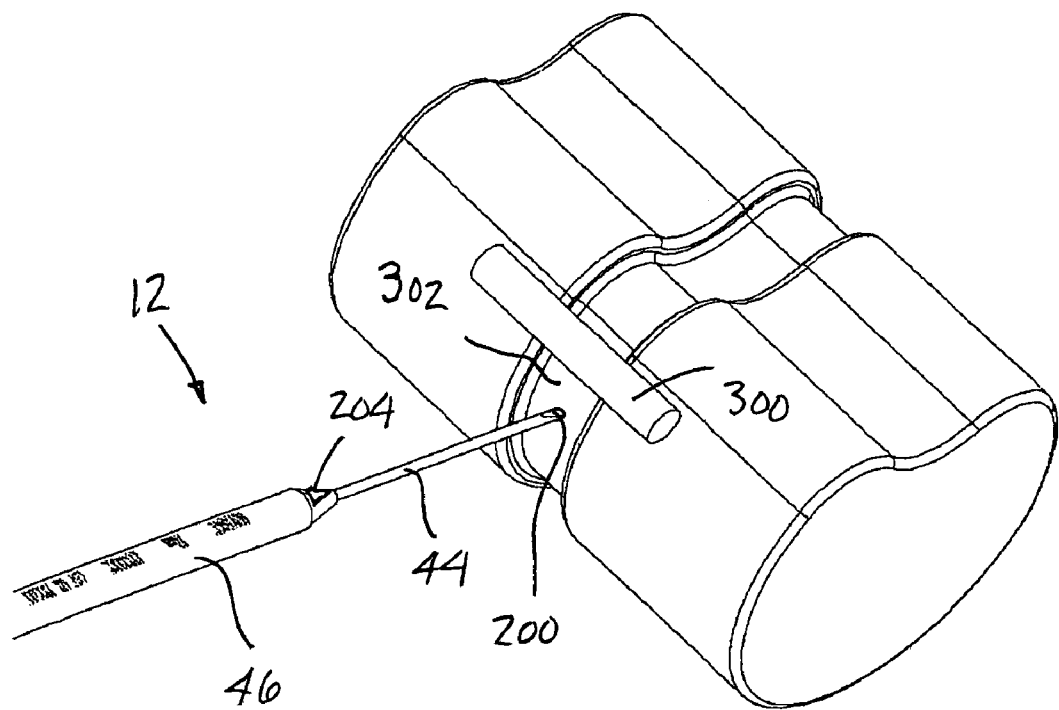
FIGS. 16-33 illustrate the various method steps (some optional) involved in accessing (by way of example only) a surgical target site in the spine according to the present invention.
Figure 17:
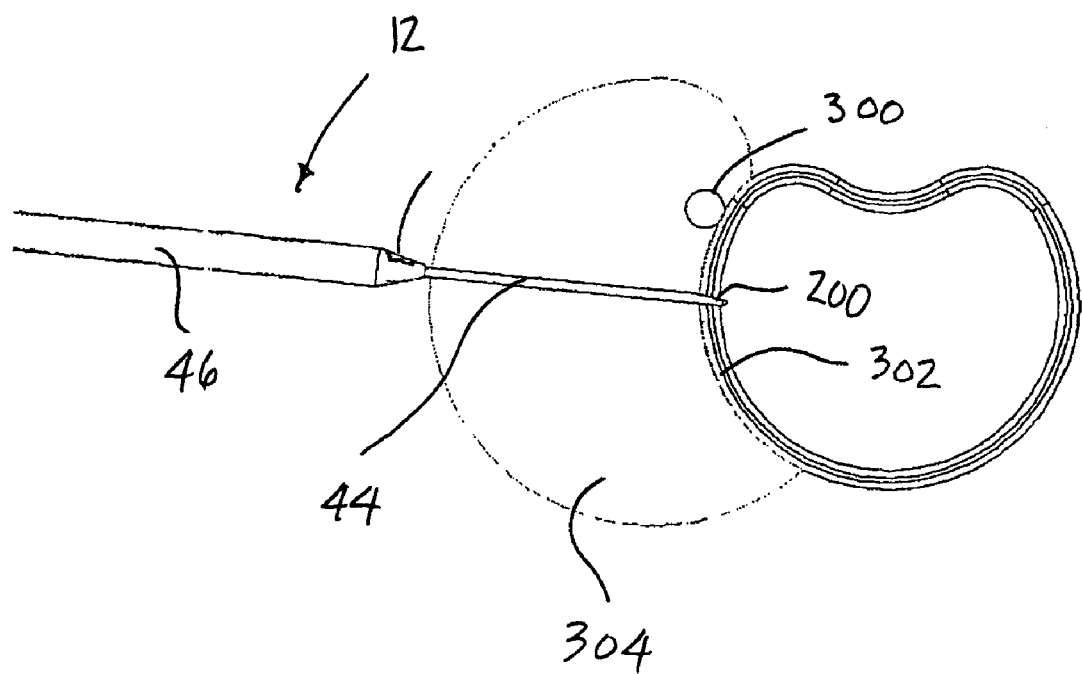

Nerve surveillance is preferably conducted during this step (via electrode 200) to monitor for the existence of (and optionally the distance and direction to) nerves or neural structures in the tissue through which the K-wire 44 must pass to reach the surgical target site. According to a preferred embodiment of the present invention, it is generally desired to advance the K-wire 44 such the distal electrode 200 is disposed a distance anterior to the exiting nerve root 300 (such as, by way of example, 10 mm). As shown in FIGS. 16-17, it is preferred to advance the K-wire 44 to the annulus 302 of the disc before advancing the inner dilator 46. This is to prevent the unnecessary distraction of the psoas muscle 304 (which must be passed through in order to approach the surgical target site in the lateral or far-lateral approach shown) in the instance significant nerves or neural structures are encountered in the initial advancement of the K-wire 44. If such nerves or neural structures are encountered, the K-wire 44 may simply be removed and re-advanced along a different approach path.

Figure 18:
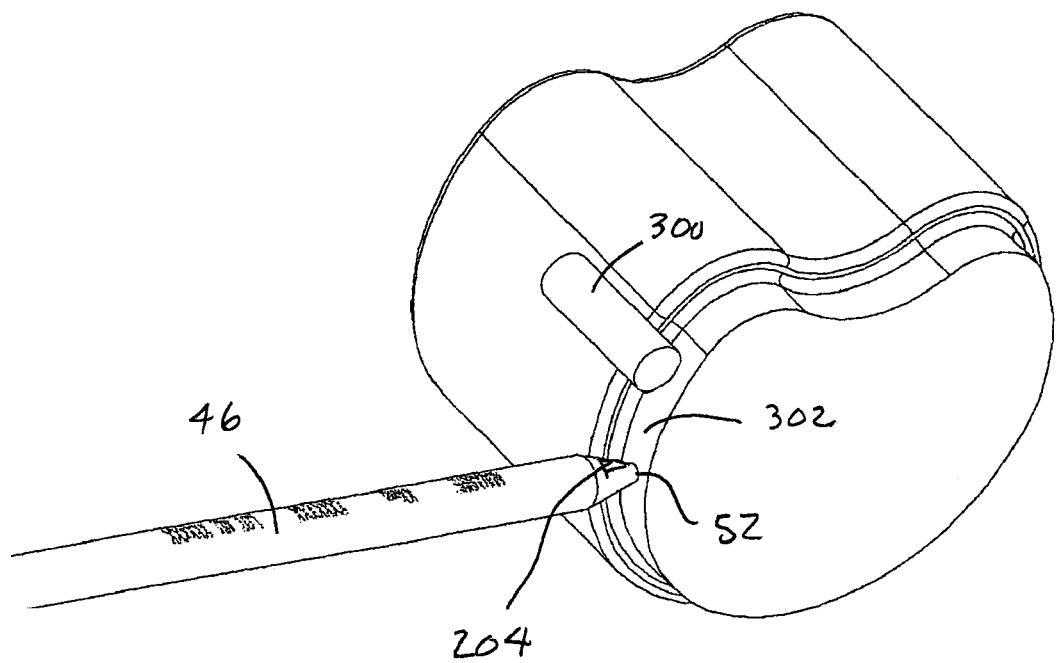
Figure 19:
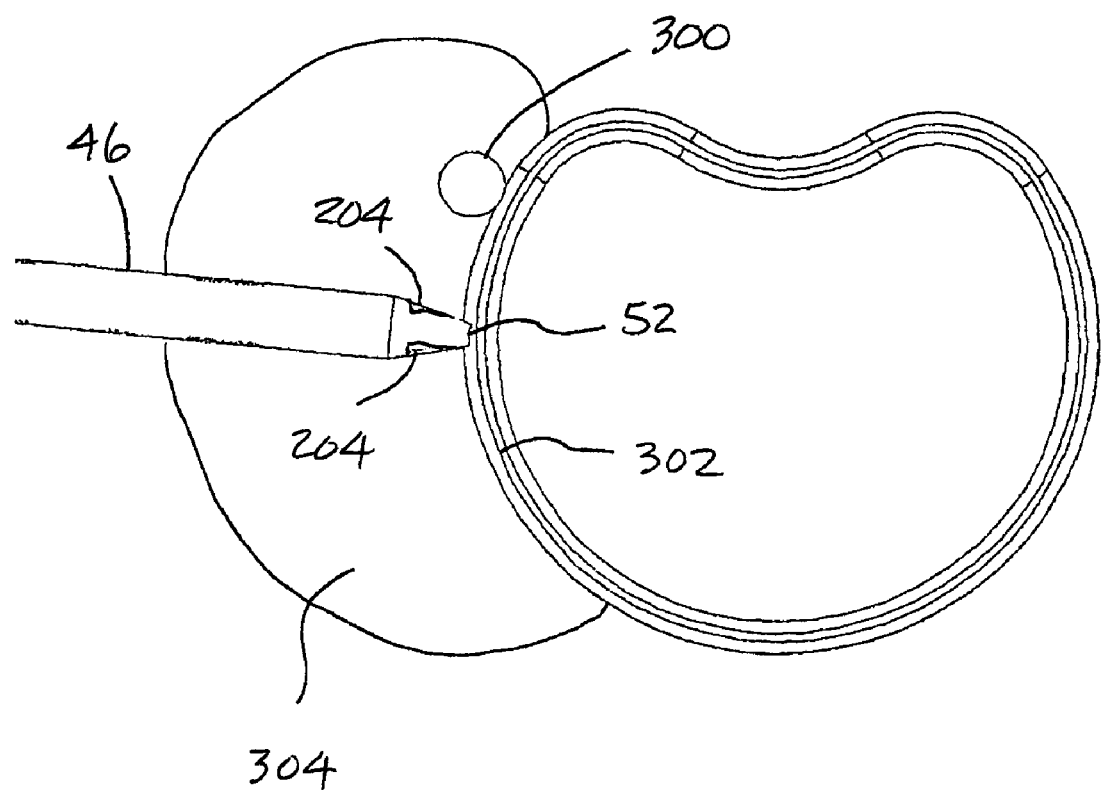
Figure 20:
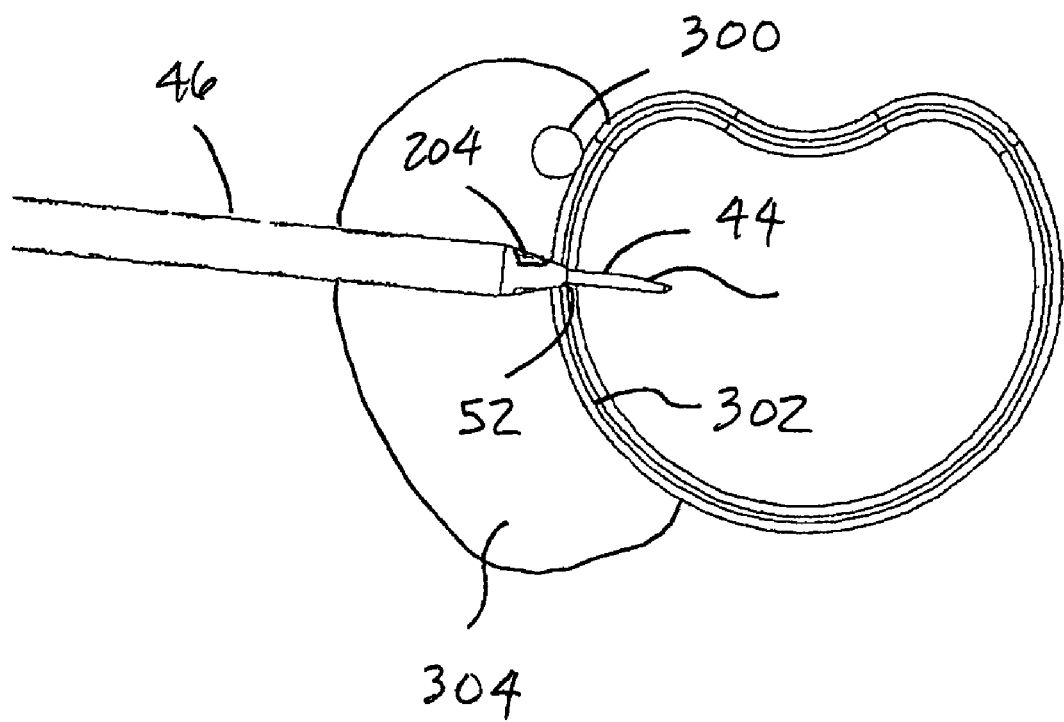

As shown in FIGS. 18-19, once the K-wire 44 is safely introduced to the surgical target site, the inner dilator 46 may thereafter be advanced over the K-wire 44 until the distal end 52 abuts the annulus 302 of the disc. Nerve surveillance is also conducted during this step (via electrode 204 shown in FIGS. 3-4) to monitor for the existence of (and optionally the distance and direction to) nerves or neural structures in the tissue through which the inner dilator 46 must pass to reach the surgical target site. Next, as shown in FIG. 22, the K-wire 44 may be advanced through the annulus 302 such that the electrode 200 is disposed within the interior (nucleus pulposis region) of the disc (such as, by way of example, an internal distance of 15 to 20 mm).

Figure 21:
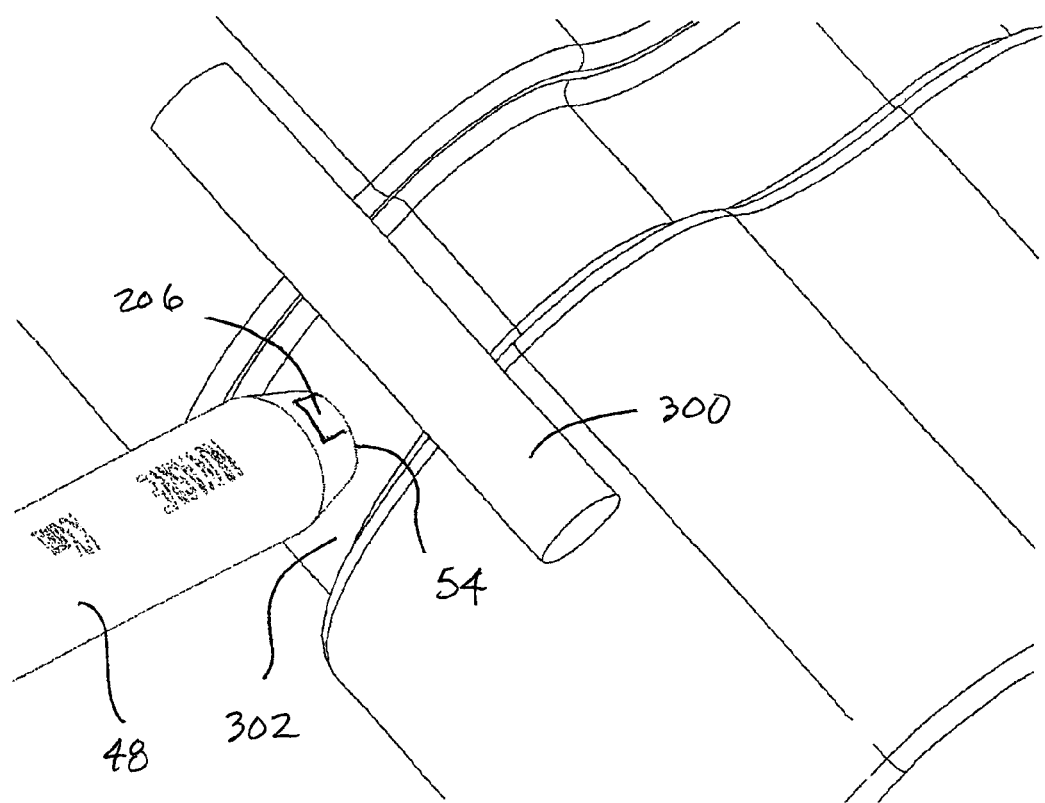
Figure 22:
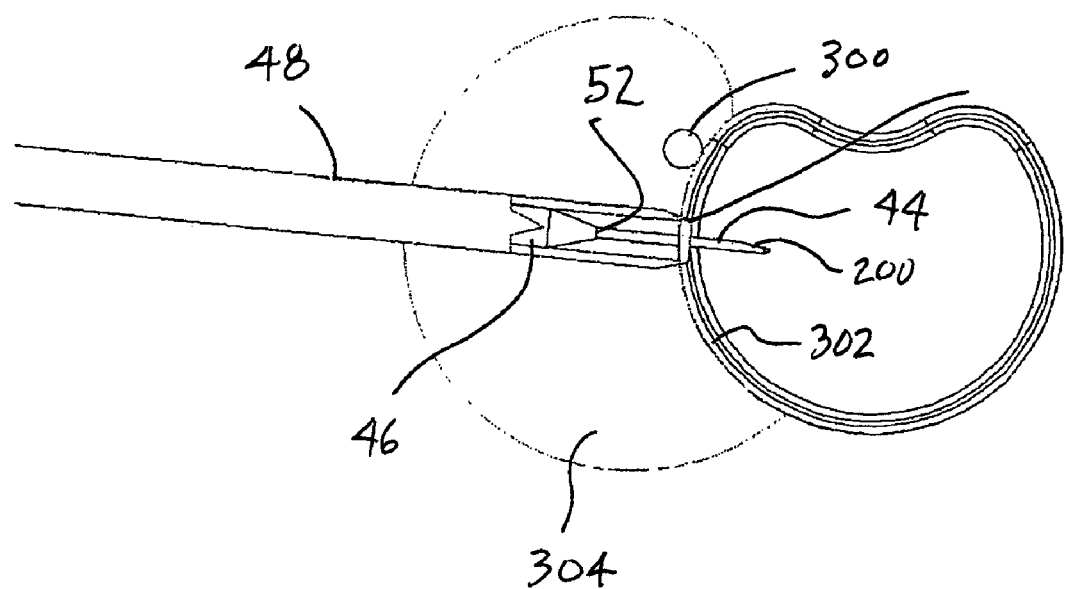

With reference to FIGS. 21-22, the outer dilator 48 is next advanced over the inner dilator 46 to further distract the tissue leading down to the surgical target site. As with the K-wire 44 and inner dilator 46, nerve surveillance is conducted during this step (via electrode 206 shown in FIGS. 3-4) to monitor for the existence of (and optionally the distance and direction to) nerves or neural structures in the tissue through which the outer dilator 48 must pass to reach the surgical target site.

Figure 23:
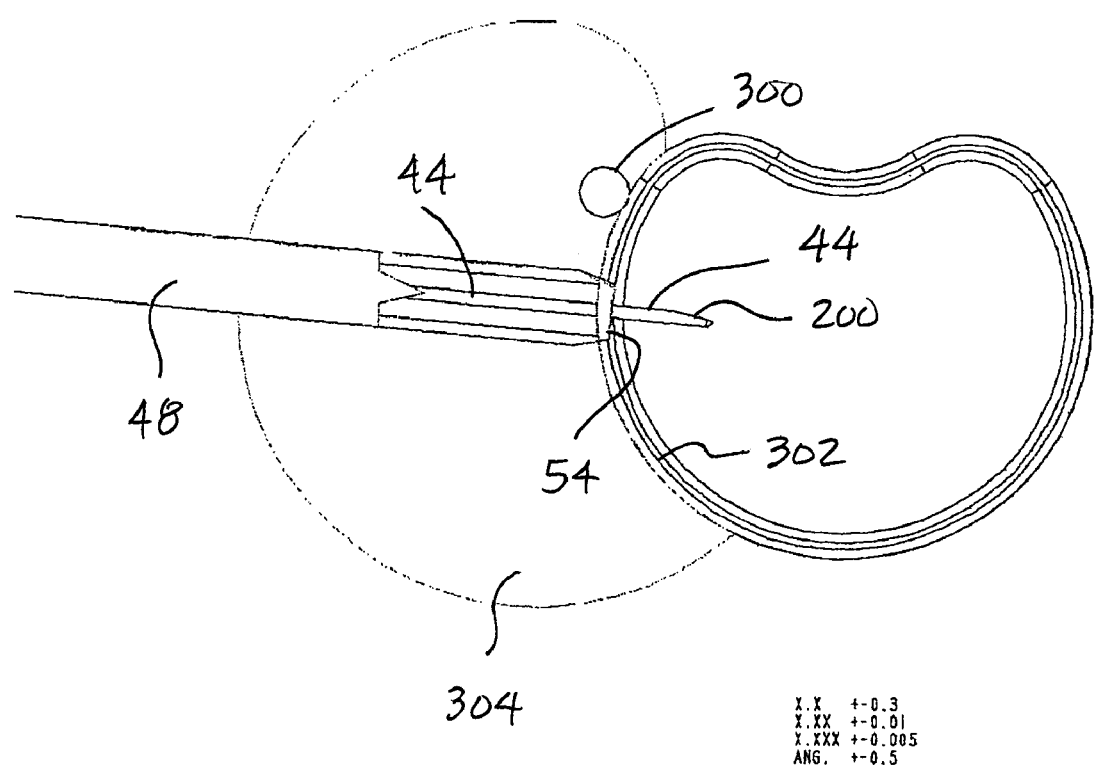
Figure 24:
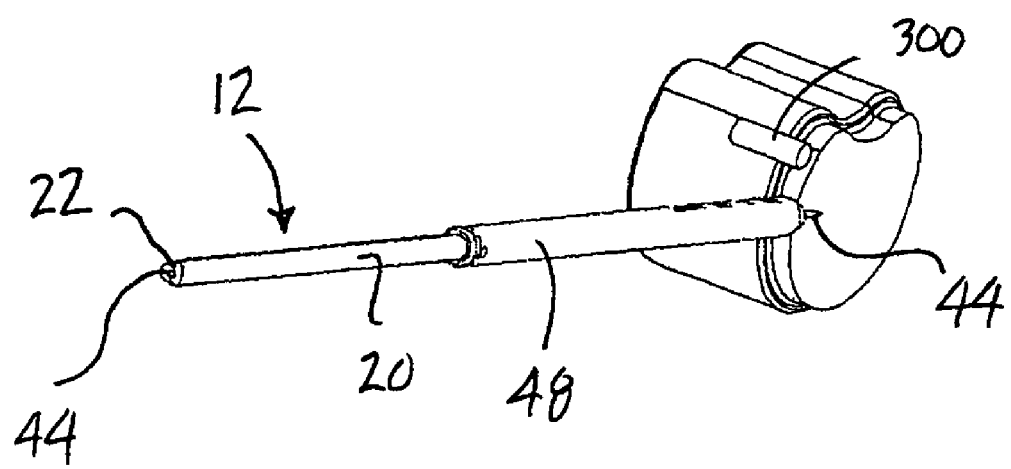
Figure 25:
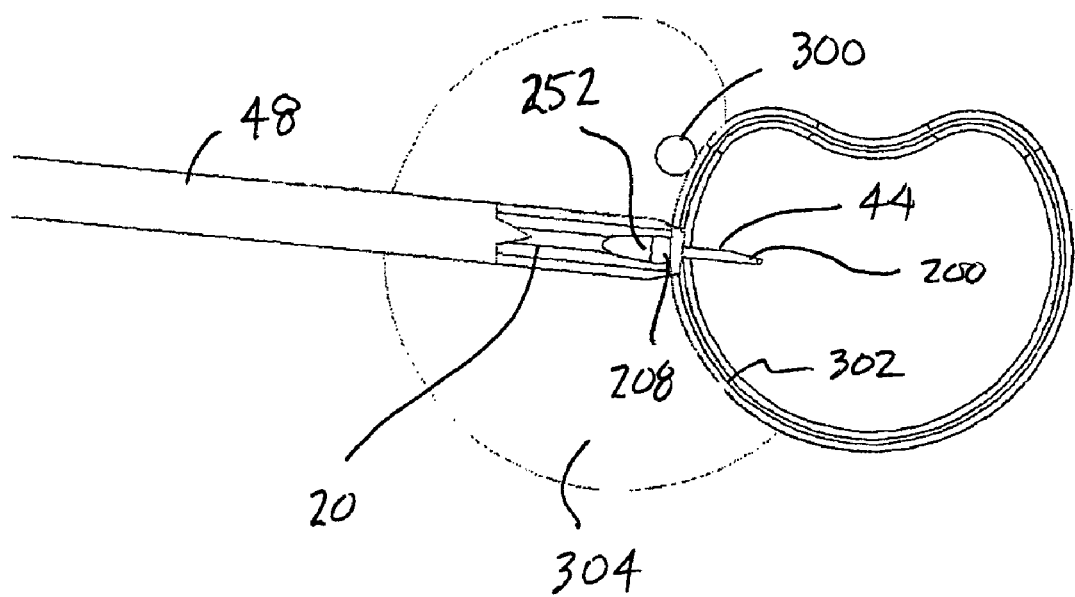

With reference to FIG. 23, the inner dilator 48 is next removed, leaving the K-wire 44 and outer dilator 48 in position. This creates a space therebetween which, in one embodiment of the present invention, is dimensioned to receive the speculum blades 20, 22 as shown in FIGS. 24-25. To accomplish this step, the speculum blades 20, 22 must be disposed in an abutting relationship so as to form an inner lumen (via corresponding grooves 88 shown in FIG. 5) dimensioned to be slideably advancing over the stationary K-wire 44. Once again, as noted above, it may be desired at this step to advance a confirmation probe down the outer dilator 48 to interrogate the tissue surrounding the surgical target site to ensure that no nerves or neural structures are present in (or have migrated into) this vicinity before the speculum blades 20, 22 are advanced into the outer dilator 48.

Figure 26:
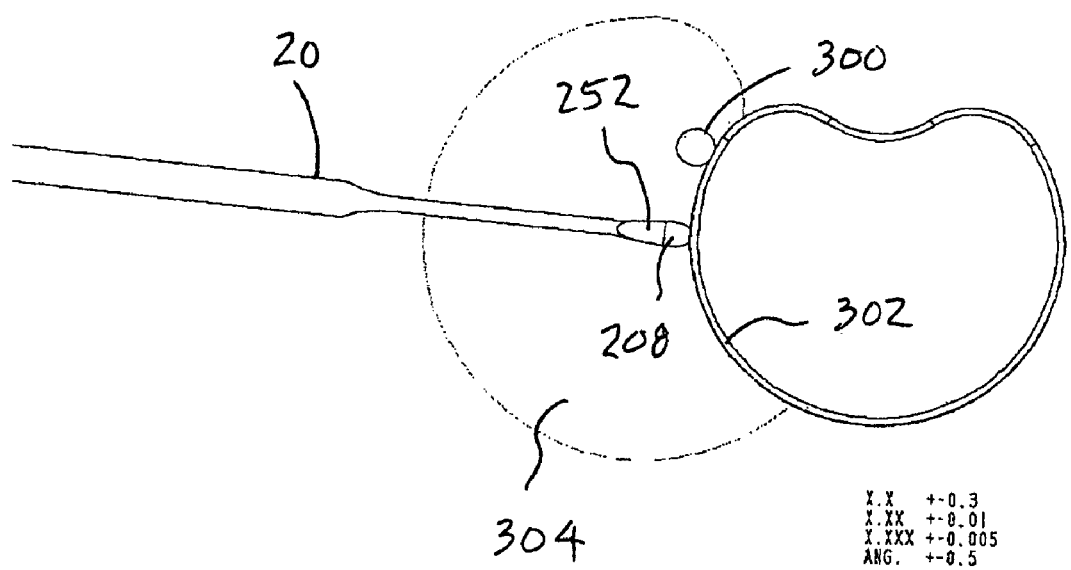
Figure 27:
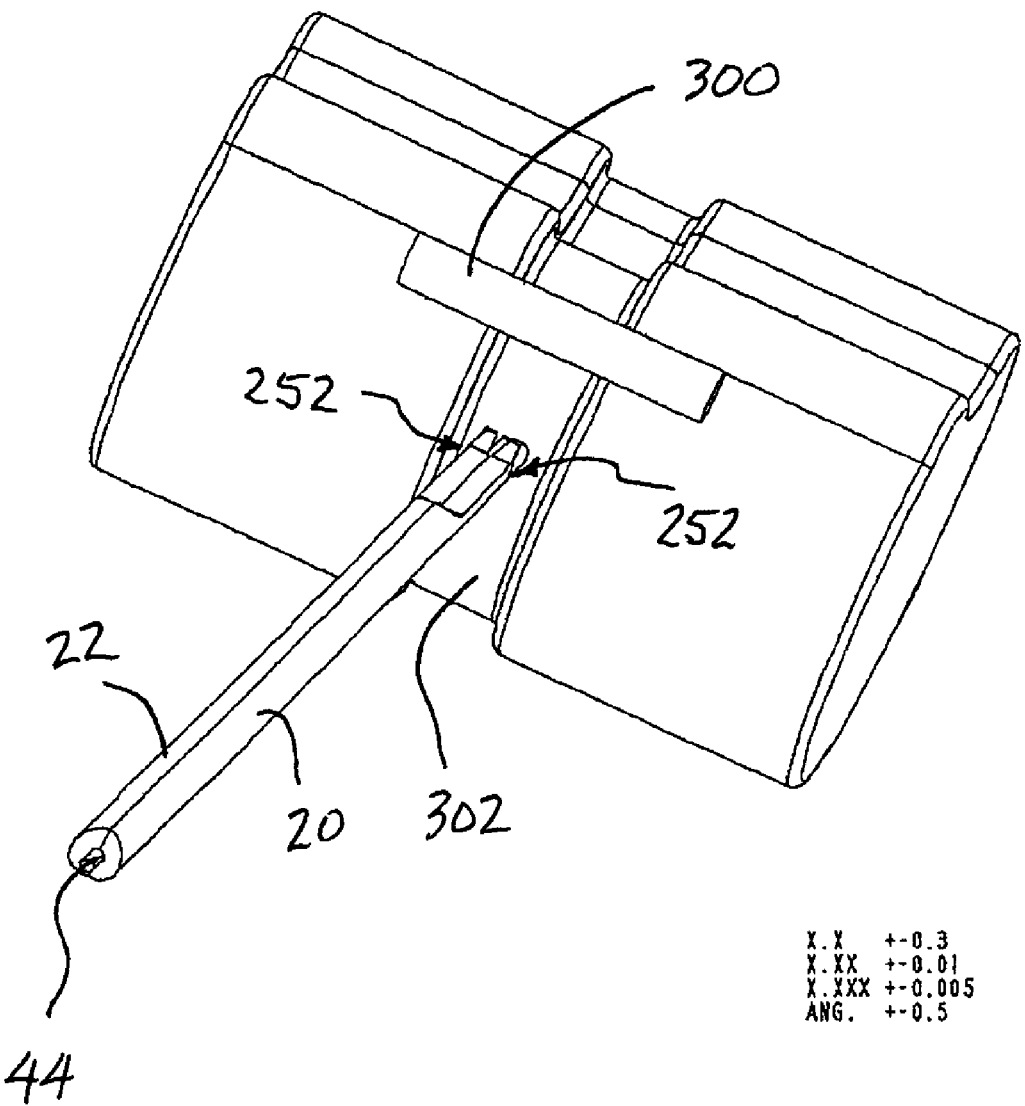
Figure 28:
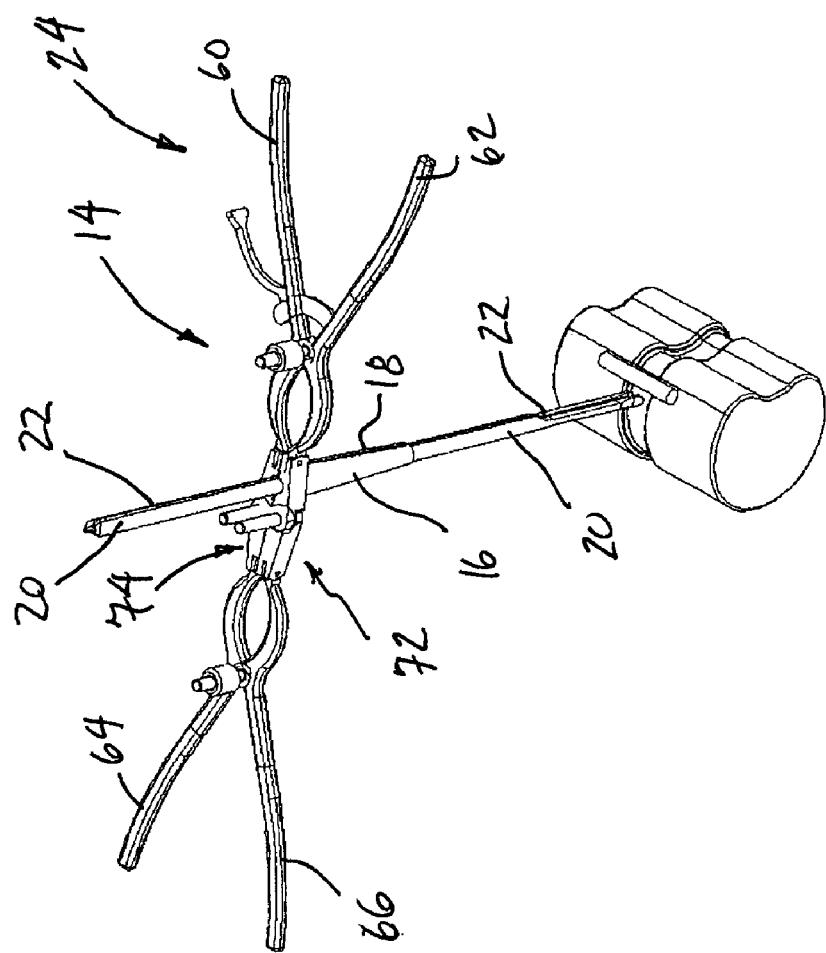
Figure 29:
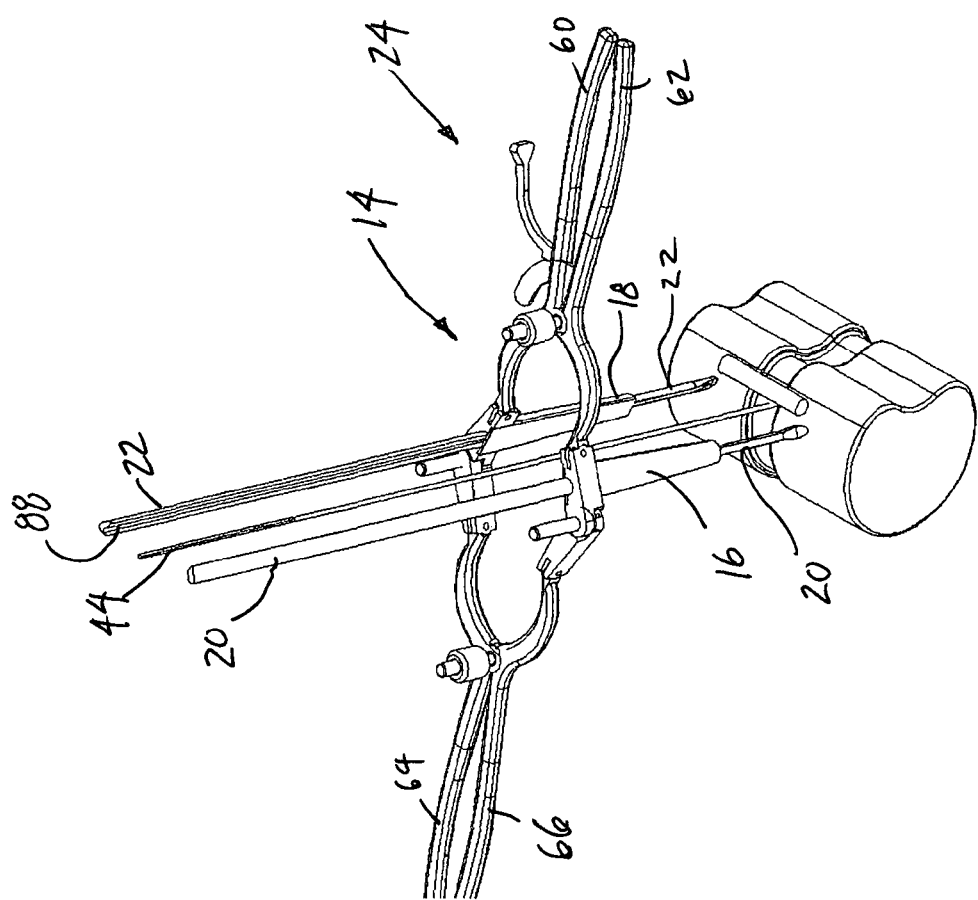

Turning to FIGS. 26-27, the outer dilator 48 may then be removed, leaving the speculum blades 20, 22 in abutting relationship within the tissue previously distracted by the outer dilator 48. As shown in FIGS. 28-29, the pivot linkage assembly 14 may be advanced such that the pivot arms 16, 18 slideably (or otherwise) pass over the speculum blades 20, 22. In one embodiment, the pivot arms 16, 18 are dimensioned such that each distal end comes into general abutment with the exterior of the psoas muscle 304. That said, it is within the scope of the invention to provide the pivot arms 16, 18 such that each distal end extends downward into the psoas 304 towards the surgical target site (which may be advantageous from the standpoint of adding rigidity to the distal portions of the speculum blades 20, 22 for the purpose of facilitating the process of secondary tissue distraction). Once positioned over the speculum blades 20, 22, the handle assembly 24 may be operate to distract tissue from the position shown in FIG. 28 to that shown in FIG. 29.

Figure 30:
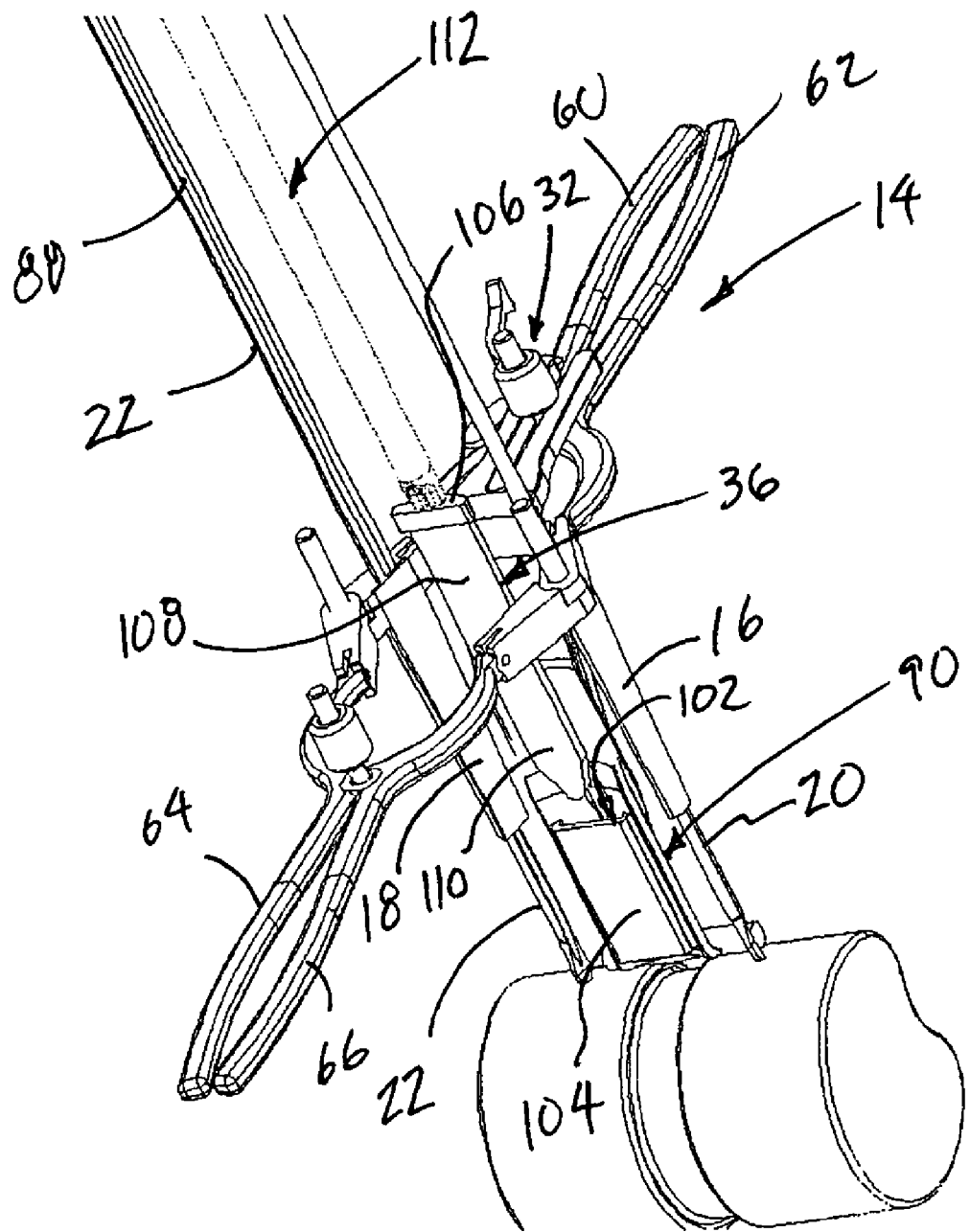
Figure 31:
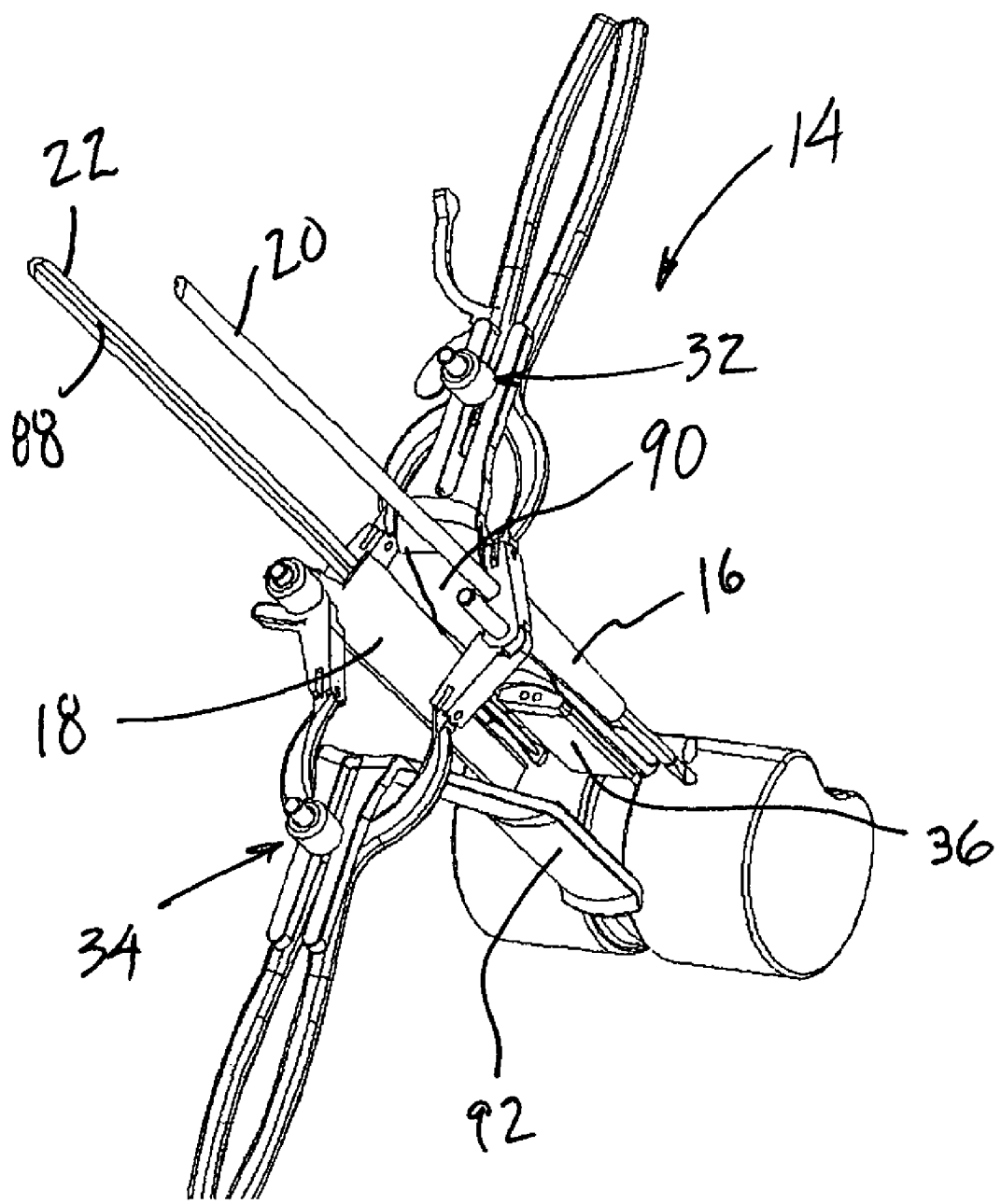
Figure 32:
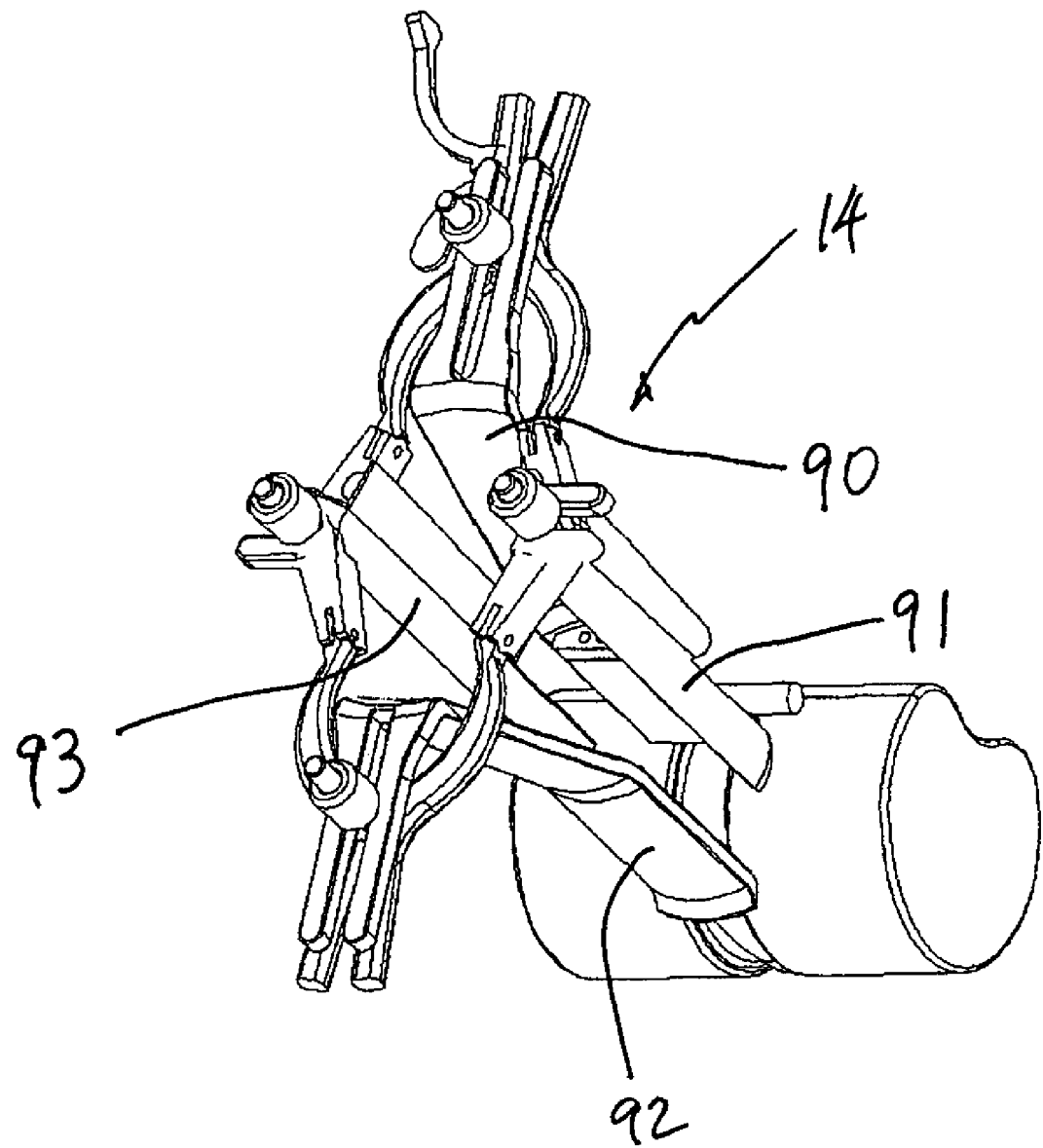

As shown in FIG. 30, the first retractor 90 is then introduced into the distracted region, positioned adjacent to the posterior region of the disc space, and locked to the pivot linkage 14 via the locking assembly 32. At that point, the locking member 36 may be advanced via the tool 112 and engaged with the retractor blade 90 such that the middle region 108 resides at least partially within the passageway 102 and the distal region 110 extends into the disc space. Thereafter, as shown in FIG. 31, the retractor blade 92 may be introduced into the distracted region, positioned adjacent to the anterior region of the disc space, and locked to the pivot linkage 14 via the locking assembly 34. At that point, another locking member 36 may be engaged in the same fashion as with the retractor blade 90, with the distal region 110 extending into the disc space. As shown in FIG. 32, additional retractor blades 91, 93 may be coupled to the pivot linkage 14 to provide retraction in the caudal and cephalad directions, respectively.

Figure 33:
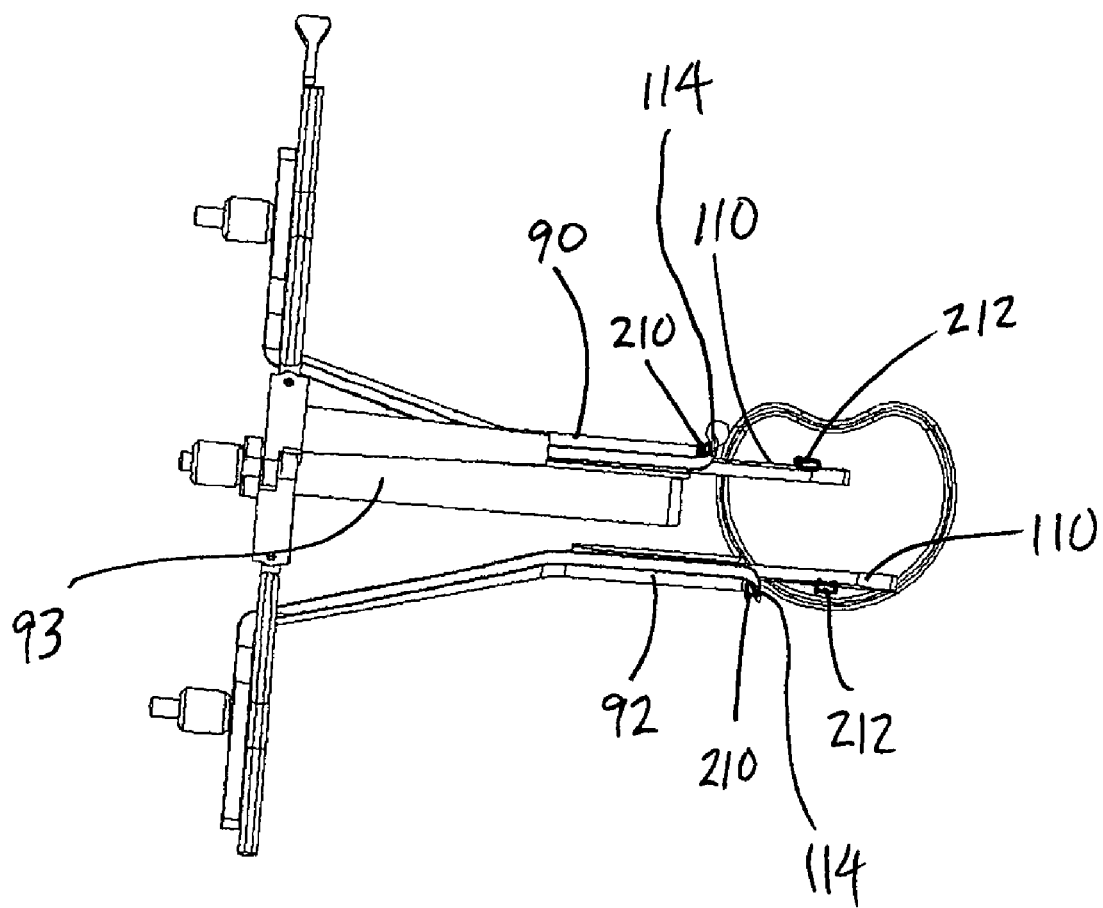

The end result is shown in FIG. 33, wherein an operative corridor has been created to the spinal target site (in this case, the disc space) defined by the retractor blades 90, 92 (and optionally 91, 93). The distal regions 110 of the locking each locking member 36 advantageously extends into the disc space to prevent the ingress of tissue (e.g., neural, vasculature, etc. . . . ) into the surgical target site and/or operative corridor and the egress of instruments or implants out of the surgical target site and/or operative corridor.

In a further protective measure, each retractor blade 90, 92 is equipped with a guard member 114 to prevent similar ingress and egress. Both guard members 114 (as well as additional regions of the distal region 110 of the locking member 36) may be provided with electrodes 210, 212, respectively, capable of performing nerve surveillance to monitor for the existence of (and optionally the distance and direction to) nerves or neural structures in the tissue or region surrounding or adjacent to these components while disposed in the general vicinity of the surgical target site. The electrode 210 on the guard member 114 of the posterior retractor blade 90, in particular, may be used to assess the status or health of the nerve root 300, especially if the nerve root 300 is in close proximity to that guard member 114. This may be performed by using the nerve status determination systems or techniques disclosed in co-pending and commonly assigned U.S. Pat. No. 6,500,128, entitled "Nerve Proximity and Status Detection System and Method," the entire contents of which is hereby incorporated by reference as is set forth fully herein.

As evident from the above discussion and drawings, the present invention accomplishes the goal of providing a novel surgical access system and related methods which involve creating a distraction corridor to a surgical target site, thereafter retracting the distraction corridor to establish and maintain an operative corridor to the surgical target site, and optionally detecting the existence of (and optionally the distance and/or direction to) neural structures before, during and/or after the formation of the distraction and/or operative corridors.

The steps of distraction followed by retraction are advantageous because they provide the ability to more easily position an operative corridor-establishing device through tissue that is strong, thick or otherwise challenging to traverse in order to access a surgical target site. The various distraction systems of the present invention are advantageous in that they provide an improved manner of atraumatically establishing a distraction corridor prior to the use of the retraction systems of the present invention. The various retractor systems of the present invention are advantageous in that they provide an operative corridor having improved cross-sectional area and shape (including customization thereof) relative to the prior art surgical access systems. Moreover, by optionally equipping the various distraction systems and/or retraction systems with one or more electrodes, an operative corridor may be established through (or near) any of a variety of tissues having such neural structures which, if contacted or impinged, may otherwise result in neural impairment for the patient.

The surgical access system of the present invention can be used in any of a wide variety of surgical or medical applications, above and beyond the spinal applications discussed herein. By way of example only, in spinal applications, any number of implants and/or instruments may be introduced through the working cannula 50, including but not limited to spinal fusion constructs (such as allograft implants, ceramic implants, cages, mesh, etc.), fixation devices (such as pedicle and/or facet screws and related tension bands or rod systems), and any number of motion-preserving devices (including but not limited to nucleus replacement and/or total disc replacement systems).

While certain embodiments have been described, it will be appreciated by those skilled in the art that variations may be accomplished in view of these teachings without deviating from the spirit or scope of the present application. For example, with regard to the monitoring system 120, it may be implemented using any combination of computer programming software, firmware or hardware. As a preparatory act to practicing the system 120 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

What is claimed is:

1. A method of accessing a surgical target site, comprising the steps of:
    creating an initial distraction corridor through tissue extending between an incision point and a surgical target site via an initial distraction assembly including a K-wire and at least one dilator capable of being slideably passed over said K-wire;
    distracting said tissue from said initial distraction corridor to a secondary distraction corridor with an instrument capable of being guided to said surgical target site along said at least one dilator of said initial distraction assembly;
    introducing a plurality of retractor blades for retracting said tissue from said secondary distraction corridor to create an operative corridor to said surgical target site; and
    providing a control unit capable of electrically stimulating at least one stimulation electrode provided on said initial distraction assembly, sensing a response of a nerve depolarized by said stimulation, determining at least one of nerve proximity and nerve direction from said initial distraction assembly to the nerve based upon the sensed response, and communicating to a user at least one of visual indicia and audio communications representing at least one of said determined nerve proximity and said determined nerve direction.

2. The method of claim 1, wherein said instrument capable of being guided to said surgical target site along said at least one dilator of said initial distraction assembly comprises a secondary distraction system.

3. The method of claim 2, wherein said secondary distraction system includes at least two speculum blades capable of being moved generally apart from one another.

4. A method of accessing a surgical target sites comprising the steps of:
    creating an operative corridor through tissue extending between an incision point and a surgical target site via a distraction assembly and a retraction assembly, wherein said distraction assembly comprises an initial assembly including an elongate inner element and at least one dilator, said distraction assembly further comprises a secondary instrument advanceable to said surgical target site along said at least one dilator of said initial assembly, and wherein at least one of said distraction assembly and retraction assembly includes at least one stimulation electrode;
    electrically stimulating said at least one stimulation electrode;
    sensing a response of a nerve depolarized by said stimulation;
    determining at least one of nerve proximity and nerve direction of said nerve relative to at least one of said distraction assembly and said retraction assembly based upon the sensed response; and
    communicating indicia to a user representing at least one of said determined nerve proximity and said determined nerve direction.

5. The method of claim 4, wherein said operative corridor is established to a spinal target site.

6. The method of claim 4, wherein said operative corridor is established to a spinal target site via a lateral, trans-psoas approach.

7. The method of claim 4, wherein communicating to a user includes displaying at least one of alpha-numeric characters, light-emitting elements and graphics representing an electromyographic (EMG) response of the muscle.

8. The method of claim 4, wherein communicating to a user includes audibly communicating sounds representing an electromyographic (EMG) response of the muscle.

9. The method of claim 4, wherein said step of determining at least one of nerve proximity and nerve direction includes determining a threshold stimulation level required to evoke said neuromuscular response and wherein said step of determining a threshold stimulation level includes establishing first a bracket containing said threshold stimulation level and bisecting said bracket to form a smaller second bracket containing said threshold stimulation level.

* * * * *